(12) United States Patent
Kiesel et al.

(10) Patent No.: US 8,723,140 B2
(45) Date of Patent: May 13, 2014

(54) PARTICLE ANALYZER WITH SPATIAL MODULATION AND LONG LIFETIME BIOPROBES

(75) Inventors: Peter Kiesel, Palo Alto, CA (US); Richard H. Bruce, Soquel, CA (US); Michael Bassler, Mainz (DE)

(73) Assignee: Palo Alto Research Center Incorporated, Palo Alto, CA (US)

( * ) Notice: Subject to any disclaimer, the term of this patent is extended or adjusted under 35 U.S.C. 154(b) by 102 days.

(21) Appl. No.: 13/206,439

(22) Filed: Aug. 9, 2011

(65) Prior Publication Data
US 2013/0037728 A1    Feb. 14, 2013

(51) Int. Cl.
*F21V 9/16*    (2006.01)

(52) U.S. Cl.
USPC ........................................ 250/458.1

(58) Field of Classification Search
USPC ........................................ 250/458.1
See application file for complete search history.

(56) References Cited

U.S. PATENT DOCUMENTS

| | | | |
|---|---|---|---|
| 3,357,230 A | 12/1967 | Topaz | |
| 3,797,911 A | 3/1974 | Kogelnik et al. | |
| 3,915,573 A | 10/1975 | Knoll et al. | |
| 3,958,252 A | 5/1976 | Kashio | |
| 3,973,118 A | 8/1976 | LaMontagne | |
| 4,081,277 A | 3/1978 | Brault et al. | |
| 4,131,899 A | 12/1978 | Christou | |
| 4,251,733 A | 2/1981 | Hirleman | |
| 4,427,296 A | 1/1984 | Demarest et al. | |
| 4,455,089 A | 6/1984 | Yeung et al. | |
| 4,514,257 A | 4/1985 | Karlsson et al. | |
| 4,536,762 A | 8/1985 | Moates | |
| 4,573,796 A | 3/1986 | Martin et al. | |
| 4,715,672 A | 12/1987 | Duguay et al. | |
| 4,730,922 A | 3/1988 | Bach et al. | |
| 4,764,670 A | 8/1988 | Pace et al. | |

(Continued)

FOREIGN PATENT DOCUMENTS

| | | |
|---|---|---|
| EP | 0354067 | 2/1990 |
| EP | 0442738 | 8/1991 |

(Continued)

OTHER PUBLICATIONS

Keisel et al. "Spatially modulated fluorescence emission from moving particles" Appl. Phys. Lett. 94, 041107 (Jan. 27, 2009).*

(Continued)

*Primary Examiner* — David Porta
*Assistant Examiner* — Edwin Gunberg
(74) *Attorney, Agent, or Firm* — Hollingsworth Davis, LLC

(57) ABSTRACT

An analyzer includes a flow cell having a flow channel through which a sample passes. A light source excites at least a first particle type in the sample in one or more excitation region(s), and a detector detects light emitted by the excited particle. A spatial filter defines detection regions, wherein light emitted by the particle is transmitted to the detector, and interspersed shielded regions, wherein such light is at least partially blocked from reaching the detector. The light emitted by the excited particle has a response time $\tau 1$, and the sample may also contain a component that is excited by the light source and that has a response time $\tau 2 < \tau 1$. The excitation region(s) and the detection regions are arranged to provide a time delay between excitation and detection, the time delay tailored to isolate light emitted by the first particle from light emitted by the component.

22 Claims, 12 Drawing Sheets

(56) References Cited

U.S. PATENT DOCUMENTS

| | | |
|---|---|---|
| 4,793,705 A | 12/1988 | Shera |
| 4,820,042 A | 4/1989 | Barger |
| 4,822,998 A | 4/1989 | Yokota et al. |
| 4,957,371 A | 9/1990 | Pellicori et al. |
| 4,959,674 A | 9/1990 | Khuri-Yakub et al. |
| 4,976,542 A | 12/1990 | Smith |
| 5,028,545 A * | 7/1991 | Soini .......................... 436/501 |
| 5,080,462 A | 1/1992 | Goto |
| 5,144,498 A | 9/1992 | Vincent |
| 5,151,585 A | 9/1992 | Siebert |
| 5,159,199 A | 10/1992 | Labaw |
| 5,166,755 A | 11/1992 | Gat |
| 5,218,426 A | 6/1993 | Hall et al. |
| 5,243,614 A | 9/1993 | Wakata et al. |
| 5,254,919 A | 10/1993 | Bridges et al. |
| 5,281,305 A | 1/1994 | Lee et al. |
| 5,305,082 A | 4/1994 | Bret |
| 5,312,535 A | 5/1994 | Waska et al. |
| 5,324,401 A | 6/1994 | Lee et al. |
| 5,370,842 A | 12/1994 | Miyazaki et al. |
| 5,394,244 A | 2/1995 | Tsai |
| 5,410,404 A | 4/1995 | Grant |
| 2,708,389 A | 5/1995 | Kavanagh |
| 5,414,508 A | 5/1995 | Takahashi et al. |
| 5,434,667 A | 7/1995 | Hutchins et al. |
| 5,437,840 A | 8/1995 | King et al. |
| 5,445,934 A | 8/1995 | Fodor et al. |
| 5,491,347 A | 2/1996 | Allen et al. |
| 5,528,045 A | 6/1996 | Hoffman et al. |
| 5,572,328 A | 11/1996 | Fouckhardt et al. |
| 5,608,517 A | 3/1997 | Munk |
| 5,631,734 A | 5/1997 | Stern et al. |
| 5,666,195 A | 9/1997 | Shultz et al. |
| 5,674,698 A | 10/1997 | Zarling et al. |
| 5,677,769 A | 10/1997 | Bendett |
| 5,682,038 A | 10/1997 | Hoffman |
| 5,745,308 A | 4/1998 | Spangenberg |
| 5,760,900 A | 6/1998 | Ito et al. |
| 5,777,329 A | 7/1998 | Westphal et al. |
| 5,784,507 A | 7/1998 | Holm-Kennedy et al. |
| 5,792,663 A | 8/1998 | Fry et al. |
| 5,793,485 A | 8/1998 | Gourley |
| 5,798,222 A | 8/1998 | Goix |
| 5,801,831 A | 9/1998 | Sargoytechev |
| 5,825,792 A | 10/1998 | Villeneuve et al. |
| 5,864,641 A | 1/1999 | Murphy et al. |
| 5,872,655 A | 2/1999 | Seddon et al. |
| 5,876,674 A | 3/1999 | Dosoretz et al. |
| 5,880,474 A | 3/1999 | Norton et al. |
| 5,917,606 A | 6/1999 | Kaltenbach |
| 5,933,233 A | 8/1999 | Gunther |
| 5,945,676 A | 8/1999 | Khalil et al. |
| 5,953,138 A | 9/1999 | Ellis |
| 5,958,122 A | 9/1999 | Fukuda et al. |
| 5,982,478 A | 11/1999 | Ainsworth et al. |
| 5,982,534 A | 11/1999 | Pinkel |
| 6,040,578 A | 3/2000 | Malin et al. |
| 6,049,727 A | 4/2000 | Crothall |
| 6,066,243 A | 5/2000 | Anderson et al. |
| 6,091,502 A | 7/2000 | Weigl et al. |
| 6,108,463 A | 8/2000 | Herron et al. |
| 6,116,718 A | 9/2000 | Peeters et al. |
| 6,122,536 A | 9/2000 | Sun et al. |
| 6,137,117 A | 10/2000 | Feldstein et al. |
| 6,169,604 B1 | 1/2001 | Cao |
| 6,187,592 B1 | 2/2001 | Gourley |
| 6,192,168 B1 | 2/2001 | Feldstein et al. |
| 6,216,022 B1 | 4/2001 | Tyrrell et al. |
| 6,249,346 B1 | 6/2001 | Chen et al. |
| 6,275,628 B1 | 8/2001 | Jones et al. |
| 6,285,504 B1 | 9/2001 | Diemeer |
| 6,295,130 B1 | 9/2001 | Sun et al. |
| 6,306,933 B1 | 10/2001 | Eiger et al. |
| 6,307,623 B1 | 10/2001 | Papuchon et al. |
| 6,310,690 B1 | 10/2001 | Cao et al. |
| 6,353,475 B1 | 3/2002 | Jensen et al. |
| 6,399,405 B1 | 6/2002 | Chen et al. |
| 6,405,073 B1 | 6/2002 | Crowley et al. |
| 6,429,022 B1 | 8/2002 | Kunz et al. |
| 6,438,397 B1 | 8/2002 | Bosquet et al. |
| 6,459,080 B1 | 10/2002 | Yin et al. |
| 6,468,702 B1 | 10/2002 | Yi et al. |
| 6,483,959 B1 | 11/2002 | Singh et al. |
| 6,490,034 B1 | 12/2002 | Woias et al. |
| 6,505,775 B1 | 1/2003 | Gu et al. |
| 6,514,460 B1 | 2/2003 | Fendrock |
| 6,519,037 B2 | 2/2003 | Jung et al. |
| 6,525,308 B1 | 2/2003 | Schmidt-Hattenberger |
| 6,558,945 B1 | 5/2003 | Kao |
| 6,577,780 B2 | 6/2003 | Lockhart |
| 6,580,507 B2 | 6/2003 | Fry et al. |
| 6,603,548 B2 | 8/2003 | Church et al. |
| 6,608,679 B1 | 8/2003 | Chen et al. |
| 6,628,390 B1 | 9/2003 | Johnson |
| 6,630,999 B2 | 10/2003 | Shroder |
| 6,639,679 B2 | 10/2003 | Frojdh |
| 6,665,113 B2 | 12/2003 | Aso et al. |
| 6,694,158 B2 | 2/2004 | Polak |
| 6,697,542 B2 | 2/2004 | Platzman et al. |
| 6,700,664 B1 | 3/2004 | Honda et al. |
| 6,704,104 B2 | 3/2004 | Li |
| 6,710,871 B1 | 3/2004 | Goix |
| 6,736,484 B2 | 5/2004 | Nakamura |
| 6,742,884 B2 | 6/2004 | Wong et al. |
| 6,747,285 B2 | 6/2004 | Schueller et al. |
| 6,755,983 B2 | 6/2004 | Yudasaka |
| 6,759,713 B2 | 7/2004 | Chabinyc et al. |
| 6,768,555 B2 | 7/2004 | Chen et al. |
| 6,781,690 B2 | 8/2004 | Armstrong et al. |
| 6,785,002 B2 | 8/2004 | Zarrabian et al. |
| 6,795,190 B1 | 9/2004 | Paul et al. |
| 6,796,710 B2 | 9/2004 | Yates et al. |
| 6,800,849 B2 | 10/2004 | Staats |
| 6,806,925 B2 | 10/2004 | Gaudiana et al. |
| 6,809,865 B2 | 10/2004 | Chen |
| 6,815,125 B1 | 11/2004 | Okabe et al. |
| 6,816,257 B2 | 11/2004 | Goix |
| 6,830,856 B2 | 12/2004 | Tsai et al. |
| 6,838,361 B2 | 1/2005 | Takeo |
| 6,839,140 B1 | 1/2005 | O Keefe et al. |
| 6,856,718 B2 | 2/2005 | Kane et al. |
| 6,865,198 B2 | 3/2005 | Barbarossa |
| 6,867,420 B2 | 3/2005 | Mathies et al. |
| 6,867,868 B1 | 3/2005 | Barbarossa |
| 6,870,149 B2 | 3/2005 | Berezin |
| 6,872,320 B2 | 3/2005 | Wong et al. |
| 6,872,588 B2 | 3/2005 | Chabinyc et al. |
| 6,887,713 B2 | 5/2005 | Nelson et al. |
| 6,890,050 B2 | 5/2005 | Ready et al. |
| 6,895,158 B2 | 5/2005 | Aylward et al. |
| 6,906,792 B2 | 6/2005 | Ortyn et al. |
| 6,927,852 B2 | 8/2005 | Reel |
| 6,934,435 B2 | 8/2005 | Kane |
| 6,952,603 B2 | 10/2005 | Gerber et al. |
| 6,972,261 B2 | 12/2005 | Wong et al. |
| 6,983,176 B2 | 1/2006 | Gardner et al. |
| 7,011,630 B2 | 3/2006 | Desai et al. |
| 7,012,696 B2 | 3/2006 | Orr et al. |
| 7,024,236 B2 | 4/2006 | Ford et al. |
| 7,027,848 B2 | 4/2006 | Robinson et al. |
| 7,034,933 B2 | 4/2006 | Walker et al. |
| 7,046,357 B2 | 5/2006 | Weinberger et al. |
| 7,057,712 B2 | 6/2006 | Beck et al. |
| 7,064,836 B2 | 6/2006 | Bechtel et al. |
| 7,065,112 B2 | 6/2006 | Ghosh et al. |
| 7,090,728 B2 | 8/2006 | Nakamura |
| 7,106,441 B2 | 9/2006 | Sun et al. |
| 7,118,660 B2 | 10/2006 | Witt |
| 7,130,321 B2 | 10/2006 | Spinelli et al. |
| 7,136,161 B2 | 11/2006 | Nakamura |
| 7,149,396 B2 | 12/2006 | Schmidt et al. |
| 7,167,239 B2 | 1/2007 | Yamamoto |
| 7,172,842 B2 | 2/2007 | Tsai et al. |
| 7,195,465 B2 | 3/2007 | Kane et al. |

(56) References Cited

U.S. PATENT DOCUMENTS

| | | |
|---|---|---|
| 7,195,797 B2 | 3/2007 | Mearini et al. |
| 7,196,796 B2 | 3/2007 | Moriya et al. |
| 7,217,574 B2 | 5/2007 | Pien et al. |
| 7,243,670 B2 | 7/2007 | Witt et al. |
| 7,248,318 B2 | 7/2007 | Nakamura et al. |
| 7,248,361 B2 | 7/2007 | Kiesel et al. |
| 7,252,360 B2 | 8/2007 | Hersch et al. |
| 7,256,888 B2 | 8/2007 | Staehr et al. |
| 7,259,856 B2 | 8/2007 | Kachanov et al. |
| 7,262,845 B2 | 8/2007 | Arrutshy |
| 7,264,973 B2 | 9/2007 | Lin et al. |
| 7,268,868 B2 | 9/2007 | Kiesel et al. |
| 7,274,011 B2 | 9/2007 | Tennant et al. |
| 7,277,569 B2 | 10/2007 | Bruce et al. |
| 7,291,824 B2 | 11/2007 | Kiesel et al. |
| 7,298,478 B2 | 11/2007 | Gilbert et al. |
| 7,305,112 B2 | 12/2007 | Curry et al. |
| 7,309,563 B2 | 12/2007 | Paul et al. |
| 7,310,153 B2 | 12/2007 | Kiesel et al. |
| 7,315,667 B2 | 1/2008 | Schmidt et al. |
| 7,355,699 B2 | 4/2008 | Gilbert et al. |
| 7,358,476 B2 | 4/2008 | Kiesel et al. |
| 7,364,996 B2 | 4/2008 | Kawase |
| 7,365,022 B2 | 4/2008 | Wong et al. |
| 7,372,435 B2 | 5/2008 | Ortyn |
| 7,386,199 B2 | 6/2008 | Schmidt et al. |
| 7,387,892 B2 | 6/2008 | Kiesel et al. |
| 7,391,517 B2 | 6/2008 | Tebbia et al. |
| 7,400,399 B2 | 7/2008 | Wawro et al. |
| 7,404,982 B2 | 7/2008 | Toyoda |
| 7,417,729 B2 | 8/2008 | Greenwald |
| 7,420,677 B2 | 9/2008 | Schmidt et al. |
| 7,433,552 B2 | 10/2008 | Kiesel et al. |
| 7,440,101 B2 | 10/2008 | Auer et al. |
| 7,456,953 B2 | 11/2008 | Schmidt et al. |
| 7,466,307 B2 | 12/2008 | Trent |
| 7,466,409 B2 | 12/2008 | Kiesel et al. |
| 7,471,393 B2 | 12/2008 | Trainer |
| 7,471,399 B2 | 12/2008 | Kiesel et al. |
| 7,479,625 B2 | 1/2009 | Kiesel et al. |
| 7,486,407 B2 | 2/2009 | Kiesel et al. |
| 7,491,552 B2 | 2/2009 | McDevitt et al. |
| 7,496,463 B2 | 2/2009 | Nicoli et al. |
| 7,497,992 B2 | 3/2009 | Cunningham et al. |
| 7,502,123 B2 | 3/2009 | Kiesel et al. |
| 7,506,268 B2 | 3/2009 | Jennings |
| 7,511,824 B2 | 3/2009 | Sebastian et al. |
| 7,521,769 B2 | 4/2009 | Cunningham |
| 7,522,786 B2 | 4/2009 | Kiesel et al. |
| 7,522,811 B2 | 4/2009 | Schmidt et al. |
| 7,524,459 B2 | 4/2009 | Adams et al. |
| 7,529,438 B2 | 5/2009 | Schmidt et al. |
| 7,545,513 B2 | 6/2009 | Kiesel et al. |
| 7,547,904 B2 | 6/2009 | Schmidt et al. |
| 7,554,673 B2 | 6/2009 | Kiesel et al. |
| 7,633,629 B2 | 12/2009 | Kiesel et al. |
| 7,641,777 B2 | 1/2010 | Joseph et al. |
| 7,661,358 B2 | 2/2010 | Kim et al. |
| 7,694,231 B2 | 4/2010 | Kocienda et al. |
| 7,695,680 B2 | 4/2010 | Unlu et al. |
| 7,701,580 B2 | 4/2010 | Bassler et al. |
| 7,701,590 B2 | 4/2010 | Kiesel et al. |
| 7,718,948 B2 | 5/2010 | Kiesel et al. |
| 7,720,554 B2 | 5/2010 | DiBernardo et al. |
| 7,733,100 B2 | 6/2010 | Kasapi |
| 7,763,856 B2 | 7/2010 | Kiesel et al. |
| 7,767,444 B2 | 8/2010 | Liu et al. |
| 7,811,438 B2 | 10/2010 | Lean et al. |
| 7,817,254 B2 | 10/2010 | Hegyi et al. |
| 7,817,276 B2 | 10/2010 | Kiesel et al. |
| 7,817,281 B2 | 10/2010 | Kiesel et al. |
| 7,830,517 B2 | 11/2010 | Beck et al. |
| 7,839,450 B2 | 11/2010 | Hing |
| 7,852,490 B2 | 12/2010 | Kiesel et al. |
| 7,879,390 B2 | 2/2011 | Saileo et al. |
| 7,879,598 B2 | 2/2011 | Zesch et al. |
| 7,894,068 B2 | 2/2011 | Bassler et al. |
| 7,936,463 B2 | 5/2011 | Kiesel et al. |
| 8,137,626 B2 | 3/2012 | Maltezos et al. |
| 8,223,127 B2 | 7/2012 | Park et al. |
| 8,338,080 B2 | 12/2012 | Kozawa et al. |
| 8,373,860 B2 | 2/2013 | Kiesel et al. |
| 8,437,582 B2 | 5/2013 | Kiesel et al. |
| 2002/0155485 A1 | 10/2002 | Kao |
| 2003/0161024 A1 | 8/2003 | Zhang et al. |
| 2003/0169311 A1 | 9/2003 | Kong Leong et al. |
| 2003/0178555 A1 | 9/2003 | Fang |
| 2004/0067167 A1 | 4/2004 | Zhang et al. |
| 2004/0141884 A1 | 7/2004 | Unno et al. |
| 2004/0175734 A1 | 9/2004 | Stahler et al. |
| 2004/0178523 A1 | 9/2004 | Kim et al. |
| 2005/0042615 A1 | 2/2005 | Smith et al. |
| 2005/0046821 A1 | 3/2005 | Hanson et al. |
| 2007/0116609 A1 | 5/2007 | Baeurle et al. |
| 2007/0145249 A1 | 6/2007 | Kiesel et al. |
| 2007/0166725 A1 | 7/2007 | McBride et al. |
| 2008/0095985 A1 | 4/2008 | Frey et al. |
| 2008/0181827 A1 | 7/2008 | Bassler et al. |
| 2008/0183418 A1 | 7/2008 | Bassler et al. |
| 2009/0195773 A1 | 8/2009 | Bassler et al. |
| 2009/0195852 A1 | 8/2009 | Bassler et al. |
| 2010/0155572 A1 | 6/2010 | Kiesel et al. |
| 2010/0155577 A1 | 6/2010 | Kiesel et al. |
| 2010/0157291 A1 | 6/2010 | Kiesel et al. |
| 2010/0201988 A1 | 8/2010 | Kiesel et al. |
| 2010/0261288 A1 | 10/2010 | Recknor et al. |
| 2011/0222062 A1 | 9/2011 | Martini et al. |
| 2013/0037728 A1 | 2/2013 | Kiesel et al. |

FOREIGN PATENT DOCUMENTS

| | | |
|---|---|---|
| EP | 0679881 | 11/1995 |
| EP | 1324018 | 7/2003 |
| EP | 1653217 | 5/2006 |
| EP | 1800752 | 6/2007 |
| EP | 1801553 | 6/2007 |
| EP | 1801562 | 6/2007 |
| EP | 1801564 | 6/2007 |
| EP | 1950552 | 7/2008 |
| JP | 02049143 | 2/1990 |
| JP | 02245638 | 10/1990 |
| JP | 03020642 | 1/1991 |
| JP | 04223261 | 8/1992 |
| JP | 04297888 | 10/1992 |
| JP | 05240774 | 9/1993 |
| JP | 06018421 | 1/1994 |
| JP | 08261922 | 10/1996 |
| JP | 2004252214 | 9/2004 |
| JP | 2005165073 | 6/2005 |
| JP | 2007518991 | 6/2007 |
| WO | WO9520144 | 7/1995 |
| WO | WO9944042 | 9/1999 |
| WO | WO9954730 | 10/1999 |
| WO | WO0039573 | 7/2000 |
| WO | WO0062050 | 10/2000 |
| WO | WO0225269 | 3/2002 |
| WO | WO2004033059 | 4/2004 |
| WO | WO2004063681 | 7/2004 |
| WO | WO2004083820 | 9/2004 |
| WO | WO2005017498 | 2/2005 |
| WO | WO2005068971 | 7/2005 |
| WO | WO2005108963 | 11/2005 |
| WO | WO2006133360 | 12/2006 |
| WO | WO2007069840 | 6/2007 |

OTHER PUBLICATIONS

Kiesel et al., "'Spatially modulated emission' advances point-of-care diagnostics", Laser Focus World, Nov. 2010, pp. 47-50.

"4-Channel Optical Transceiver Applying 3-Dimensional Polymeric Waveguide", FIND, vol. 24, No. 4, 2006, pp. 1-5.

Adams et al., "Microfluidic Integration on Detector Arrays for Absorption and Fluorescence Micro-spectrometer", Sensors and Actuators, 2003, pp. 25-31.

(56) References Cited

OTHER PUBLICATIONS

Agilent Technologies, "Agilent 83453B High-Resolution Spectrometer—Technical Specifications", Feb. 2005, pp. 1-8.
Agilent Technologies "Developing Technology: HPLC-Chip/MS", May 25, 2011, 2 pages.
Bassler et al., "Class Identification of Bio-Molecules Based on Multicolor Native Fluorescence Spectroscopy", International Journal of High Speed Electronics and Systems, vol. 17, Issue 4, 2007, pp. 671-680.
Becker et al., "Polymer Microfabrication Methods for Microfluidic Analytical Applications", Electrophoresis, vol. 21, 2000, pp. 12-26. (abstract only).
Bernini et al., "Silicon Micromachined Hollow Optical Waveguides for Sensing applications", IEEE Journal on Selected Topics in Quantum Electronics, vol. 8, No. 1, Jan./Feb. 2002, pp. 106-110. (abstract only).
Bhatta et al., "Rapid Identification of Microorganisms by Intrinsic Fluorescence", Proc. Of SPIE, vol. 5699, 2005, pp. 9-18.
Cheung et al., "Impedance Spectroscopy Flow Cytometry: On-Chip Label-Free Cell Differentiation", Cytometry Part A, vol. 65A, 2005, pp. 124-132.
Cunningham et al., "Label-Free Assays on the Bind System", Journal of Biomolecular Screening, vol. 9, No. 6, 2004, pp. 481-490.
Devasenathipathy et al., "3 Electrokinetic Flow Diagnostics", in Breuer K.S. Ed. Micro-and Nano-Scale Diagnostic Techniques, Springer Verlag, New York, 2003, pp. 121-166.
Fuhr, "Measuring with Light", Sensors Magazine Online, May 2000, 11 pages.
Fuji-Keizai USA, "Biosensor Market, R&D and Commercial Implication", 2004, 5 pages.
Gooddard et al., Anti-resonant reflecting optical waveguides (ARROW), as optimal optical detectors for micro TAS applications, printed from dias.umist.ac.uk on Aug. 1, 2005, pp. 1-5.
Henry et al., "Wavelength Response of Thin-Film Optical Position-Sensitive Detectors", J. Opt. A: Pure Appl. Opt., Vole. 4, 2002, pp. 527-534. (abstract only).
Holmes et al., "Label-Free Differential Leukocyte Counts Using a Microfabricated, Single-Cell Impedance Spectrometer", Sensors, 2007 IEEE, pp. 1452-1455. (abstract only).
Johnson et al., "Introductions to Photonic Crystals: Bloch's Theorem, Band Diagrams, and Gaps (But No Defects)", Feb. 3, 2003, 16 pages.
Johnson, "Photonic Crystals: Periodic Surprises in Electromagnetism", printed from ab-initio.mit.edu on Oct. 5, 2006, 29 pages.
Jones et al., "Dielectrophoretic Liquid Actuation Nanodroplet Formation", Journal of Applied Physics, vol. 89, No. 2, 2001, pp. 1441-1448. (abstract only).
Kalvaram et al., "Precision moulding techniques for optical waveguide devices", SPIE, vol. 3135, 1997, pp. 2-11. (abstract only).
Kim et al., "Polymer-Planar-Lightwave-Circuit-Type Variable Optical Attenuator Fabricated by Hot Embossing Process" ETRI Journal, vol. 27, No. 1, Feb. 2004, pp. 122-125.
Konsziela, "Accurately Measure Laser Spectral Characteristics", 2006, 5 pages.
Law et al., "Low-Voltage Superlattice Asymmetric Fabry-Perot Reflection Modulator", IEEE Phot. Tech. Lett, vol. 3, No. 4, Apr. 1991, pp. 324-326. (abstract only).
Liang et al., "Refractive Index Measurement of Single Living Cell Using a Biophotonic Chip for Cancer Diagnosis Applications", $9^{th}$ International Conference on Miniaturized Systems for Chemistry and Life Sciences, Oct. 2005, pp. 464-466.
Liu et al., "Nanowell Surface Enhanced Raman Scattering Arrays Fabricated by Soft-Lithography for Label-Free Biomolecular Detections in Integrated Microfluidics", Applied Physics Letters, vol. 87, 2005, pp. 1-3.
McNichols et al., "Optical Glucose Sensing in Biological Fluids: An Overview", Journal of Biomedical Optics, vol. 5, No. 1, Jan. 2000, pp. 5-16. (abstract only).
Murata, "Spectral Images Camera Using Linear Variable Interference Filter", Oct. 2003, 6 pages.
"Optical Chopper—SR540—Optical Chopper System", Stanford Research Systems, Oct. 2008, 2 pages.
Schaefer et al., "Accuracy of Position Detection Using a Position-Sensitive Detector", IEEE Transactions on Instrumentation and Measurement, vol. 47, No. 4, Aug. 1998, pp. 914-919. (abstract only).
Schmidt et al., "Enhanced light-target interaction using a novel anti-resonant waveguide concept", SPIE Proc. 6094, 2006, pp. 80-89.
Schmidt et al., "Fluorescence Spectrometer-on-a-fluidic-chip", Lab Chop, 2007. (abstract only).
Schmidt et al., "Guiding Light in Fluids", applied Physics Letters, vol. 88, 2006, pp. 151109-1-1151109-14.
Seamer et al., "Sheath Fluid control to Permit Stable Flow in Rapid Mix Flow Cytometry", Cytometry, vol. 5699, 2005, pp. 75-79.
Sims et al., "Analysis of Single Mammalian Cells On-Chip", Lab Chip., vol. 7, Issue 4, Apr. 2007, pp. 423-40. (Abstract only).
Singh et al., "Analysis of Cellular Structure by Light Scattering Measurements in a New Cytometer Design Based on a Liquid-Core Waveguide", IEEE Proceedings Nanobiotechnology, vol. 151, No. 1, Feb. 2004, pp. 10-16.
Sivaprakasam et al., "Multiple UV Wavelength Excitation and Fluorescence of Bioaerosols", $2^{nd}$ Joint conference on Point Detections, Williamsburg, VA 2004, 10 pages.
Spear et al., "Low noise position sensitive detector for optical probe beam deflection measurements", Rev. Sci. Instrum., vol. 67, No. 7, Jul. 1996, pp. 2481-2484. (abstract only).
SRU Biosystems, Inc., "BIND Biosensor TM Technology", Apr. 3, 2004 excerpt, 1 page.
Udd, "Good Sense", SPIE's OEMagazine, Aug. 2002, pp. 27-29.
Vogel, "Tunable Liquid Crystal Fabry-Perot Filters", Institute for Electrical and Optical Communication Engineering, University of Stuttgart, 2002, 10 pages. (abstract only).
Vollmer et al., "Multiplexed DNA Quantification by Spectroscopic Shift of Two Microsphere Cavities", Biophysical Journal, vol. 85, Sep. 2005, pp. 1974-1979.
Weismann et al., "Singlemode polymer waveguides for optical backplanes", Electronics Letters, vol. 32, No. 25, Dec. 5, 1996, pp. 2329-2330. (abstract only).
Xu et al., "Research of Image Spectrometer Using Linear Variable Interference Filter", Spectroscopy and Spectral Analysis, vol. 22, No. 5, p. 713-717. Oct. 2002.
File History for EP Application No. 06126524.5 as retrieved from the European Patent Office electronic file system on Dec. 19, 2012, 140 pages.
File History for U.S. Appl. No. 11/698,409.
File History for U.S. Appl. No. 11/698,338.
File History for U.S. Appl. No. 13/113,021.
File History for EP Application No. 09151643.5 as retrieved from the European Patent Office electronic file system on Aug. 14, 2013, 149 pages.
File History for EP Application No. 09151644.3 as retrieved from the European Patent Office electronic file system on Aug. 14, 2013, 109 pages.

\* cited by examiner

PARTICLE ANALYZER WITH SPATIAL MODULATION AND LONG LIFETIME BIOPROBES

TECHNICAL FIELD

This application relates generally to techniques for performing sample analysis by exposing the sample to electromagnetic radiation and by evaluating electromagnetic radiation emitted by the sample. The application also relates to components, devices, systems, and methods pertaining to such techniques.

BACKGROUND

Various techniques have been proposed for performing sample analysis using light emanating from objects. For example, U.S. Pat. No. 7,358,476 (Kiesel et al.) discusses a fluidic structure with a channel along which is a series of sensing components to obtain information about objects traveling within the channel, such as droplets or other objects carried by a fluid. A sensing component includes a set of cells that photosense a range of photon energies that emanate from objects. A processor receives information about objects from the sensing components and uses it to obtain spectral information. Additional techniques are described, for example, in U.S. Patent Application Publications 2008/0181827, and 2008/0183418 and U.S. Pat. Nos. 7,701,580; 7,894,068; and 8,373,860.

Also, various flow cytometry techniques have been proposed.

BRIEF SUMMARY

We have developed a new family of sample analysis devices, and related components, systems, and methods, that involve illuminating a sample with excitation light from at least one light source, and detecting light that emanates from the sample. The sample typically includes, or is suspected to include, components such as particles that respond differently to excitation light from the light source. A first particle or particle type may emit light having a characteristic response time $\tau 1$, and a second particle or other component of the sample may emit light having a characteristic response time $\tau 2 < \tau 1$. The disclosed devices and methods allow for detection of the first particle with reduced interference from the second particle or other component (including but not limited to scattered excitation light, or background light due to native fluorescence from same or other particles, or from a fluid, a transport medium, or fluidic chip material, for example) by introducing a delay between excitation of the sample with the light source and detection of the emitted light by the detector. The delay is tailored so that light emission from the other component, e.g., unwanted autofluorescence from the sample, is substantially decayed by the time the sample enters a detection region, but light emission from the first particle, e.g., fluorescence from a cell of interest tagged with a fluorescent dye, persists at a level that can be detected in that detection region. In combination with this technique, spatial filtering is included to provide interspersed detection regions and shielded regions so that light emanating from the first particle impinges on a detector in an intermittent fashion to provide a time-varying detector output. The spatial filtering may involve placing a patterned mask between a flow channel, through which the sample passes, and the detector. In many cases a single detector, rather than an array or other plurality of detectors, can be used. Analysis of the time-varying detector output can be used to provide information about the composition of the sample. In many cases, the disclosed techniques can be practiced in compact analyzers of robust design, suitable for use in point-of-care (POC) testing.

We therefore disclose, among other things, analyzers that include a flow cell having a flow channel through which a sample passes. A light source excites at least a first particle type in the sample in one or more excitation region(s), and a detector detects light emitted by the excited particle. A spatial filter defines detection regions, in which light emitted by the particle is transmitted to the detector, and interspersed shielded regions, in which such light is at least partially blocked from reaching the detector. The light emitted by the excited particle has a response time $\tau 1$, and the sample may also contain a component that is excited by the light source and that has a response time $\tau 2 < \tau 1$. The excitation region(s) and the detection regions are arranged to provide a time delay between excitation and detection, the time delay tailored to isolate light emitted by the first particle from light emitted by the component. Such analyzers can, for example, allow for the clean detection of bioprobe fluorescence by ensuring that autofluorescence has substantially decayed by the time the sample enters the detection region, but that the tag fluorescence is high at the time the sample enters the detection region, the tag fluorescence preferably substantially persisting throughout the detection region.

We also disclose apparatuses for analyzing a sample that include at least a flow channel through which the sample can pass, a first light source, a detector, and a spatial filter. The first light source is adapted to illuminate one or more first excitation region(s) of the flow channel with first excitation light, the first excitation light adapted to stimulate a first light emission from particles of a first particle type. The first light emission may have a characteristic first response time $\tau 1$. For example, if the excitation light were suddenly turned off, the first light emission may decay exponentially with time t in substantial accordance with the function $e^{-t/\tau 1}$. The detector is disposed to receive light from a plurality of first detection regions of the flow channel, and the detector may provide a detector output based on the received light. The spatial filter may be disposed between the flow channel and the detector, and may have a pattern of variable transmission such that (a) the first light emission from a given first particle of the first particle type is transmitted to the detector when the given first particle is disposed in any of the first detection regions of the flow channel, and (b) the first light emission from the given first particle is at least partially blocked from reaching the detector when the given first particle is disposed in any of a plurality of first shielded regions of the flow channel, the first shielded regions being interspersed with the first detection regions. The first detection regions are preferably spatially separated from the first excitation region(s).

In at least some cases, the one or more first excitation region(s) may be a single unitary excitation region. Such single unitary excitation region may be separated from a nearest one of the first detection regions by a first gap dimension that is small enough so that the first light emission remains high enough for detection when a given first particle enters such nearest first detection region. If the apparatus is configured to pass the sample through the flow channel at a range of operating speeds having a minimum speed smin, the first gap dimension may be less than $\tau 1 *$smin. (Thus, for example, the tag fluorescence for a slow-moving particle of interest would have an intensity, when entering the detection area, greater than about 37% of its initial intensity; desirably, such intensity would be close to 100%.) Furthermore, the collection or group of first detection regions may span a length that is short enough so that the first light emission remains detectable over all of these detection regions, even at a minimum operational flow speed. For example, if the first detection regions collectively span a length L1 along the flow channel, L1 may be made to be less than $2*\tau1*smin$. (Thus, for example, the tag fluorescence for a slow-moving particle of interest may have an intensity, when exiting the last detection region, greater than about 14% (or, for example, greater than about 10%) of its initial intensity; desirably, such intensity would be substantially greater than 10% or 14% of its initial intensity, e.g., in a range of 30-50% or more.) The apparatus may be configured to isolate the first light emission from an interfering second light emission. The second light emission may be emitted by a component in the sample when exposed to the first excitation light, and the second light emission may be characterized by a second response time $\tau2$ shorter than $\tau1$. The first gap dimension is preferably large enough so that the second light emission decays to a negligible level when the component enters the nearest first detection region. For example, if the apparatus is configured to pass the sample through the flow channel at a range of operating speeds having a maximum speed smax, the first gap dimension may be greater than $\tau2*smax$.

In at least some cases, the one or more first excitation region(s) may be a plurality of first excitation regions interspersed with the first detection regions. At least one of the first excitation regions may be separated from a nearest one of these first detection regions by a first gap dimension, and the first gap dimension may be tailored to be small enough so that the first light emission remains high enough for detection when a given first particle enters such nearest first detection region, even at a minimum operational flow speed. For example, if the apparatus is configured to pass the sample through the flow channel at a range of operating speeds having a minimum speed smin, the first gap dimension may be less than $\tau1*smin$. Furthermore, the length of the first detection regions may be tailored to be short enough so that the first light emission remains detectable over each of these first detection regions, even at the minimum operational flow speed. For example, if the first detection regions have respective longitudinal dimensions along the flow channel, and a maximum value of such respective longitudinal dimensions is Lmax, then Lmax may be less than $2*\tau1*smin$. (Thus, for example, the tag fluorescence for a slow-moving particle of interest may have an intensity, when exiting the longest detection region, greater than about 14% (or, for example, greater than about 10%) of its initial intensity when it entered such detection region; desirably, such intensity would be substantially greater than 10% or 14% of its initial intensity, e.g., in a range of 30-50% or more.) The apparatus may be configured to isolate the first light emission from an interfering second light emission. The second light emission may be emitted by a component in the sample when exposed to the first excitation light, and the second light emission may be characterized by a second response time $\tau2$ shorter than $\tau1$. The first gap is preferably large enough so that the second light emission decays to a negligible level when the component enters the nearest first detection region, even at a maximum operational flow speed. For example, if the apparatus is configured to pass the sample through the flow channel at a range of operating speeds having a maximum speed smax, the first gap dimension may be greater than $\tau2*smax$.

In some cases, the detector may be further disposed to receive light from one or more second detection regions of the flow channel, which second detection regions may be interspersed with the first detection regions and the first shielded regions. Also, the pattern of variable transmission of the spatial filter may be further configured such that the first light emission from the given first particle is transmitted to the detector if the given first particle is disposed in any of the second detection regions of the flow channel. Unlike the first detection regions, the one or more second detection regions may overlap with the plurality of first excitation regions. If desired, this technique can be used to differentiate, for example, fluorescence tags having different lifetimes. One embodiment utilizing this technique is described below in connection with FIGS. 12 and 13. It will be apparent from the discussion below that if a periodic transmission function is used for the spatial filter 1226 the frequency analysis (e.g. FFT) of the signal in FIG. 13 will allow the device to determine whether the particle is tagged with a short, long, or very long lifetime probe. Thus, rather than (or in addition to) distinguishing between fluorescent tags having different emission wavelengths or colors, the device can distinguish between fluorescent tags having different lifetimes. In some cases, this technique can also be used to study simultaneously both tag fluorescence and native fluorescence from a particle of interest.

In some cases, the spatial filter may be configured such that the first excitation regions are substantially fully shielded from the detector by the spatial filter.

In some cases, the detector may be a first detector and the spatial filter may be a first spatial filter, and the first excitation light may also be also adapted to stimulate a second light emission from particles of a second particle type, the second light emission having a characteristic second response time $\tau2$. The apparatus may in such cases further include a second detector, different from the first detector, and a second spatial filter, different from the first spatial filter. The second detector may be disposed to receive light from a plurality of second detection regions of the flow channel, and may provide a second detector output based on the received light. The second spatial filter may be disposed between the flow channel and the second detector, and may have a second pattern of variable transmission such that (a) the second light emission from a given second particle of the second particle type is transmitted to the second detector if the given second particle is disposed in any of the second detection regions of the flow channel, and (b) the second light emission from the given second particle is at least partially blocked from reaching the second detector if the given second particle is disposed in any of a plurality of second shielded regions of the flow channel, the second shielded regions being interspersed with the second detection regions. The second detection regions may be spatially separated from the first excitation region(s). Alternatively, the second detection regions may at least partially overlap with, and may substantially coincide with, the first excitation region(s).

We also disclose methods of analyzing a sample, such methods preferably including: passing the sample through a flow channel; exposing the sample to excitation light in one or more first excitation region(s) of the flow channel, the excitation light being effective to stimulate a first light emission from particles of a first particle type in the sample, the first light emission having a characteristic first response time $\tau1$; transmitting the first light emission from a given first particle of the first particle type to a detector when the given first particle is disposed in any of a plurality of first detection regions of the flow channel, the first detection regions being spatially separated from the first excitation region(s); and at least partially blocking the first light emission from the given first particle from reaching the detector when the given first particle is disposed in any of a plurality of first shielded regions of the flow channel, the first shielded regions being interspersed with the first detection regions. The methods may also include providing a detector output of the detector based on light received by the detector, and providing information about the sample based on the detector output.

For the given first particle, the exposing may occur before the transmitting and the at least partially blocking. For the given first particle, the transmitting may be initiated a delay time after an end of the exposing, and the delay time may be short enough so that the transmitted first light emission remains high enough for detection. For example, the delay time may be less than τ1. The method may also be configured to isolate the first light emission from a second light emission emitted by a component in the sample when exposed to the first excitation light, the second light emission being characterized by a second response time τ2 shorter than τ1. The delay time may be tailored to be long enough so that any transmitted second light emission decays to a negligible level to avoid detection. For example, the delay time may be greater than τ2. (Thus, for example, fluorescence for the unwanted component may have an intensity, after the delay time, of less than about 37% of its initial intensity; desirably, such intensity would be close to 0% of its initial intensity.)

For the given first particle, the transmitting may occur over a time period that is short enough so that the transmitted first light emission remains high enough for detection. For example, if the time period begins when the transmitting begins and ends when the transmitting ends, and the time period may be less than 2*τ1. (Thus, for example, fluorescence for a particle of interest may have an intensity, at the end of the transmitting time period, greater than about 14% (or, for example, greater than about 10%) of its initial intensity at the beginning of such time period; desirably, such intensity would be substantially greater than 10% or 14% of its initial intensity, e.g., in a range of 30-50% or more.)

In some cases, the one or more first excitation regions may include a plurality of first excitation regions, and for the given first particle, the exposing may then be interspersed with the transmitting and the at least partially blocking. The transmitting may in some cases further include transmitting the first light emission from the given first particle when the given first particle is disposed in any of one or more second detection regions of the flow channel. The second detection regions may be interspersed with the first detection regions and the first shielded regions, and the one or more second detection regions may overlap with the plurality of first excitation regions.

In some cases, the excitation light may also be effective to stimulate a second light emission from particles of a second particle type in the sample. The method may then further include: transmitting the second light emission from a given second particle of the second particle type to a second detector when the given second particle is disposed in any of a plurality of second detection regions of the flow channel; and at least partially blocking the second light emission from the given second particle from reaching the second detector when the given second particle is disposed in any of a plurality of second shielded regions of the flow channel, the second shielded regions being interspersed with the second detection regions.

Related methods, systems, articles, and components are also discussed.

These and other aspects of the present application will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

In the figures, like reference numerals designate like elements.

DETAILED DESCRIPTION OF ILLUSTRATIVE EMBODIMENTS

The strategic landscape for biological and biomedical testing and analysis is undergoing a transformation. Today, the majority of tests are performed at major, centralized clinical laboratories. This is in part because compact, robust, and inexpensive instruments for point of care (POC) testing are not available. Principal drivers for POC testing are reducing costs, obtaining timely test results, lowering mortality rates, and reducing morbidity. Commercial flow cytometers are sophisticated analytical instruments extensively used in research and clinical laboratories. They do not, however, meet the challenging practical requirements of POC testing.

In conventional flow cytometry, the size of the excitation area is restricted approximately to the size of the particle to be detected. In contrast, the techniques disclosed herein may use a much larger excitation region to increase the total flux of detected light that emanates from a particle of interest. In combination with the large excitation area, spatial filtering can be employed to enable a high spatial resolution in the micron range. This may allow for independently detecting and characterizing particles with a separation (in the flow direction) that can approach the dimension of individual particles. Also, the disclosed techniques can be intrinsically tolerant to background fluorescence originating from fluorescent components in solution, fluorescent components of the detection apparatus, and surface contaminants.

Figure 1:
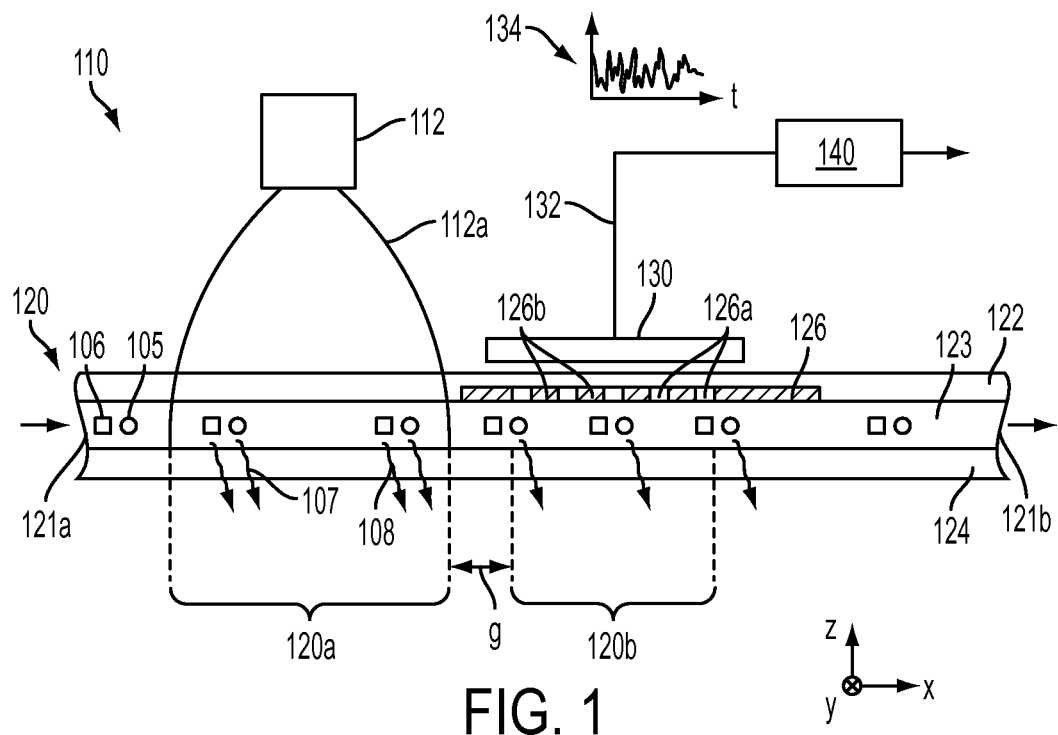
FIG. 1 is a schematic side or sectional view of a sample analyzer.

An illustrative sample analyzer 110 is shown schematically in FIG. 1, in the context of a Cartesian x-y-z coordinate system for reference purposes. The analyzer includes a light source 112, a fluid handling device 120, a spatial filter 126, and a detector 130. The fluidic device 120 is adapted to receive a sample of interest to be analyzed. The sample may enter the device 120 at an inlet 121a thereof and exit the device 120 at an outlet 121b thereof, flowing generally along the x-direction through a flow channel 123 formed between confining members 122, 124. The members 122, 124 may be or comprise plates or sheets of glass, plastic, or other suitable materials. One or both of members 122, 124 may be a microscope slide or a microscope cover glass, or portion thereof. The members 122, 124 need not, however, be planar in shape. For example, they may be portions of a unitary tube or pipe of circular cross section. Other non-planar shapes are also contemplated. In some cases, confinement of the sample may not be necessary, whereupon one or both of members 122, 124 may be omitted.

At least a portion of the confining member 122 is transmissive to excitation light emitted by the light source 112. In that regard, light source 112 may emit excitation light in a light beam 112a towards the fluidic device 120. The excitation light may comprise light of a first wavelength $\lambda 1$; in some cases, the excitation light may have a peak output at the wavelength $\lambda 1$. In many cases it is desirable for the excitation light to be relatively narrow band light, such as the light emitted by typical laser sources, but broadband light may also be used. Extremely narrow bandwidth light (such as that of certain narrow linewidth laser sources) is not necessary in general. In some cases, for example, the light source 112 may comprise a conventional light emitting diode (LED) source or a resonant cavity LED (RC-LED) source, which may emit light in a bandwidth (measured in terms of full width at half maximum, or FWHM) of 5 to 60 nm, for example. If desired, the light source may incorporate one or more filters to narrow or otherwise tailor the spectrum of the resultant output light.

Whichever type of light source is selected, the spectral makeup or composition of the excitation light emitted by the source 112 is preferably tailored to excite at least particles of a first type that may be present in the sample, as discussed further below.

The confining member 122 transmits the light beam 112a such that it illuminates the sample disposed within the flow channel 123. Illumination of the sample by the light beam 112a is limited, whether by shaping the beam 112a with suitable lenses or other optical components, and/or by masking the beam 112a with a suitable aperture or mask, to a first excitation portion or region 120a of the flow channel 123. In the embodiment of FIG. 1, the excitation portion 120a is a single unitary excitation region of the flow channel 123, with substantially no other portions or regions of the channel 123 being illuminated by the light source 112. The sample is depicted as containing two types of particles: first particles 105, and second particles 106. "First" and "second" will be understood to be arbitrary terms used for identification purposes only, and are not intended to be limiting. The first particles 105 are assumed to be particles whose presence in the sample is sought to be detected and quantified by the analyzer 110. The second particles 106, on the other hand, are assumed to be particles or any other component of the sample that, in the case of FIG. 1, is not of interest, the presence of which is not sought to be detected or quantified by the analyzer 110. In some cases, for example, the second particles may be or comprise a sub-volume of the carrier fluid that exhibits autofluorescence. In some cases, the "first particle" and "second particle" may represent different portions of a single physical body, e.g., the first particle may represent a tagged portion of a single cell and the second particle may represent a different portion of that same cell. (In some embodiments, discussed further below, the analyzer may be designed to detect and quantify the presence of the second particles also, or of other particles.) Nevertheless, we assume that both the first particles 105 and the second particles 106 are excited by the excitation light 112a, such that they emanate light 107, 108 respectively. Light emission from the particles is depicted only schematically in the figure, but the reader will understand that a given excited particle typically emits light in all directions. In conventional analyzers, the light 108 emitted by the second particles 106 might ordinarily interfere with the detection of light 107 emitted by the first particles. The light 108 might for example constitute relatively strong autofluorescence arising from second particles 106 or from any other component of the sample, while the light 107 might constitute a weaker fluorescent emission from first particles such as cells that are tagged with a particular fluorescent dye.

The term "particle" will be understood by the reader to refer broadly to an object of interest to be detected. In most applications, particles of interest are relatively small, and may be microscopic in size. A given particle of interest may be or include one or a collection of biological cell(s), virus(es), molecule(s), sub-molecular complex(es), bead(s) (including microbeads), droplets (e.g. oil in water), gas bubbles, or other bit(s) of matter, for example. Cells or other particles may be treated, e.g., stained or tagged with a suitable fluorescent probe or other agent, in such a way that they emit light in a predictable fashion when illuminated with excitation light. In this regard, the light emitted by a given excited particle may be fluorescent in nature, or it may constitute a form of scattered light such as in the case of Raman scattering. The reader will therefore understand that when we refer to, for example, incident light that is effective to excite a particle, such incident excitation light may be selectively absorbed by the particle so as to cause the particle to fluoresce, or such incident excitation light may selectively interact in some other way with the particle, e.g. so as to cause resonant Raman scattering. In any case, the emitted light is preferably shifted in wavelength to some extent relative to the excitation light so that at least a portion of the emitted light can be at least partially isolated from the excitation light with one or more suitable emission filters.

We assume that the light 108 emitted by the second particles has at least one characteristic that differs from that of the light 107 emitted by the first particles, and the analyzer 110 is designed to exploit that difference. In particular, we assume that the characteristic response times of light 107, 108 are different. More specifically, we assume that light 107 has a characteristic first response time $\tau 1$, and that light 108 has a characteristic second response time $\tau 2$, and that the first response time is greater than (i.e., longer than, or slower than) the second response time: $\tau 1 > \tau 2$. The characteristic response time of a given type of emanating light is a measure of how fast the emanating light decays after the excitation is lowered. For example, if the excitation light were suddenly turned off, the emanating light may decay exponentially with time t in substantial accordance with the function $e^{-t/\tau}$, where $\tau$ is the characteristic response time of the emanating light.

In some cases, the light 107 may differ from the light 108 in other ways also. For example, the light 107 may have spectral characteristics that differ from those of light 108. The light 107 may, for example, occur in a first spectral band and the light 108 may occur in a different second spectral band. In such cases, it may be feasible to use an optical filter in combination with a photosensitive detector to attenuate light in the second spectral band relative to light in the first spectral band, so as to reduce the contribution of the second light 108 on the detector output relative to the contribution of the first light 107. In some cases, however, the spectral characteristics of light 107, 108 may have little or no differences, so that such an optical filter may not be usable.

In the figure, the excitation light 112a is depicted as exciting both the first particles 105 and the second particles 106 residing in the excitation region 120a, causing such excited particles to emanate light 107, 108 respectively in response to the excitation. This light emission is shown as occurring in the excitation region 120a. Recall that the particles are being carried by the sample through the channel 123, generally from left to right from the perspective of FIG. 1. As each particle travels in this fashion, it eventually exits the region 120a of the flow channel and enters an adjacent gap region before entering a series of detection regions located generally in a detection zone 120b in FIG. 1. As each excited particle crosses the boundary separating the excitation region 120a from the gap region, it experiences an abrupt step change in excitation. More particularly, the excited particle goes from being fully illuminated with excitation light 112a in region 120a to being exposed to little or no excitation light in the gap region. Therefore, the amount of light emanating from an excited particle begins to decay as a function of time and position in the gap region.

The gap region may be considered to extend from the downstream boundary of the excitation region 120a to the upstream boundary of the first detection region in the detection zone 120b, as explained further below. The gap region may be defined by a suitably sized opaque film or coating on the confining member 122, or by any other suitable obstruction, or simply by shaping the beam 112a so as to avoid illuminating the gap region. The gap region is preferably sized to have a longitudinal dimension "g" along the direction of flow, i.e., along the x-axis as shown in FIG. 1. As a given excited particle traverses this distance g, light emanating from the particle decreases or decays. Assuming such a particle travels with a speed "s" along the x-axis, and assuming light emanating from the particle decays exponentially with a characteristic response time "$\tau$", the intensity or flux of light emitted by the particle decays from a relative value of 1 (or 100%) at the beginning of the gap region to a relative value of $e^{-(g/(s*\tau))}$ at the end of the gap region. Advantageously, we may tailor the analyzer 110, and in particular the longitudinal dimension g of the gap region, so that light emanating from the second particles has a negligible intensity or flux, and light emanating from the first particles has a significant intensity or flux, at the time such particles enter the detection zone 120b.

In most practical systems, the sample and its constituent particles and other components may flow through the channel 123 over some finite range of operational speeds during operation of the analyzer, e.g., between the limits of a minimum speed smin and a maximum speed smax. In order to ensure that light emanating from the second particles has decreased to a negligible intensity or flux at the moment such particles exit the gap region, even at the fastest operational speed, we may tailor the system such that $g > \tau 2 * smax$, where $\tau 2$ is the characteristic response time of the light 108 emanating from such second particles. (Thus, for example, the fluorescence from even a fast-moving unwanted component may have an intensity, when entering the detection area, of less than 37% of its initial intensity; desirably, $g > 2 * \tau 2 * smax$, so that such intensity would be less than 14% of its initial intensity, or more desirably, $g > 4.5 * \tau 2 * smax$, so that such intensity would be less than 1% of its initial intensity. These conditions may be readily achieved for substances whose unwanted autofluorescence has a lifetime $\tau 2$ in a range from 1 to 100 nanoseconds, and for substances of interest whose fluorescence has a lifetime $\tau 1$ of about 100 microseconds or more.) On the other hand, in order to ensure that light emanating from the first particles has an intensity or flux that is relatively high at the moment such particles exit the gap region, even at the slowest operational speed, we may tailor the system such that $g < \tau 1 * smin$, where $\tau 1$ is the characteristic response time of the light 107 emanating from such first particles. (Thus, for example, the tag fluorescence for a slow-moving particle of interest may have an intensity, when entering the detection area, of greater than 37% of its initial intensity; desirably, $g < 0.5 * \tau 1 * smin$, so that such intensity would be greater than 61% of its initial intensity, or more desirably, g is even less, so that such intensity would be close to 100% of its initial intensity.)

Upon exiting the gap region, the particles enter the detection zone 120b of the flow channel 123. In this zone, light emanating from excited particles is alternately transmitted to a photosensitive detector 130 and (at least partially) blocked from being transmitted to such detector, the alternating transmitting and blocking taking place as a result of a spatial filter 126 being placed between the detector 130 and the flow channel 123. The spatial filter 126 is configured with a pattern of variable transmission, such as a plurality of transmitting portions 126a and a plurality of shielding portions 126b. As an excited particle passes through the detection zone 120b of the flow channel 123, it passes through detection regions, in which emanating light is transmitted through a given one of the transmitting portions 126a to the detector 130, and it passes through shielded regions, in which emanating light is at least partially blocked from the detector 130 by a given one of the shielding portions 126b. The alternating transmitting and blocking of the emanating light produces a time variation in the detector output 132. An exemplary (idealized) time-varying output signal 134 is shown in FIG. 1. A signal processing unit 140 can be used to evaluate the detector output signal, and provide a measure of at least the first particles in the sample based on the evaluation.

At the same time light from an excited particle is being alternately transmitted and blocked from reaching the detector as the particle passes through the detection zone 120b, the intensity or flux of the excited particle's emanating light is also monotonically decreasing in accordance with such particle's characteristic response time $\tau$. Preferably, the analyzer 110 is designed such that light emanating from an excited particle that we wish to measure, such as a "first particle", remains at detectable levels throughout the detection zone 120b, even at the slowest operation flow speed (smin) of the analyzer. To ensure this, we may configure the analyzer such that $L1<2*\tau1*smin$, where $\tau1$ is the characteristic response time of the light emitted by the first particle, and L1 is the length along the flow channel of the collective set of all first detection regions defined by the spatial filter. Thus, for example, the tag fluorescence for a slow-moving particle of interest may have an intensity, when exiting the final one of the first detection regions, greater than about 14% (or, for example, greater than about 10%) of its initial intensity when it entered the initial one of the first detection regions; desirably, such intensity would be substantially greater than 10% or 14% of its initial intensity, e.g., in a range of 30-50% or more. For purposes of FIG. 1, we may consider L1 to also equal the length of the detection zone 120b as measured along the x-axis, the detection zone extending from the upstream boundary of the detection region located at the upstream end of the spatial filter (which boundary also coincides with the downstream boundary of the gap region) to the downstream boundary of the detection region located at the downstream end of the spatial filter.

If the detector 130 is placed on the same side of the flow channel 123 (relative to the z-axis) as the light source 112, as shown in FIG. 1, then the confining member 122, or at least a portion thereof, substantially transmits at least the emanating light 107 originating from the various excited first particles in the flow channel. The transmitted emanating light is also then selectively transmitted by the spatial filter 126 as discussed above and intercepted by the photosensitive detector 130, which converts the intercepted light into a current, voltage, or other measurable parameter. In exemplary embodiments, the detector 130 is a single large area detector that provides only one output, such output varying in time in accordance with the light impinging on the active surface of the detector. In other cases, the detector may include a plurality or array of distinct photosensitive devices. In any case, the detector collects light emanating from excited particles residing in specific bounded portions, referred to as a detection portions, of the flow channel. The detection portions of the flow channel may be determined or defined as a function of the size and placement of the detector, design details of the flow channel, design details of the spatial filter, and the presence of any lenses, mirrors, masks, apertures, or other optical components not shown in FIG. 1 that may be placed between the detector and the flow channel, and so forth. In the embodiment of FIG. 1, the detection portions of the flow channel are all spatially separated from the excitation region 120a of the flow channel. Thus, just as little or no excitation light is present in the gap region of the flow channel, little or no excitation light is also present in the detection zone 120b. However, in other cases discussed elsewhere herein, the detection portions may include first detection portions that are spatially separated from the excitation region(s), and second detection portions that at least partially overlap with the excitation region(s).

Exemplary photosensitive detectors that may be used in the disclosed systems, depending on the design specifications of the analyzer, include robust solid-state devices such as conventional photodiodes and avalanche photodiodes (APDs). Silicon photodiodes are responsive over a wavelength range from roughly 300 nm to 1.1 microns, and are plentiful, rugged, reliable, and relatively inexpensive. Numerous other types of photodiodes are also available, such as germanium, indium gallium arsenide (InGaAs), and extended-InGaAs, to name only a few. If desired, any other type of photosensitive detector may also be used, including, for example, one or more photomultiplier tubes. The detector may be of hybrid design, and in that regard may include one or more preamplifiers, thermoelectric coolers, and/or other features or capabilities. In many cases, the detector 130 may have an inherent responsivity that makes it responsive both to light 107 emanating from first particles 105 and to light 108 emanating from second particles 106, such that the detector does not have any ability to inherently distinguish between such emanating light. For this reason, some or all of the detection regions are spatially separated from the excitation region(s) as discussed elsewhere herein in order to remove or reduce the contribution of light emanating from the second particles on the detector output, or in some cases, to allow the signal processing unit to distinguish between light emanating from the second particles from light emanating from the first particles.

In many cases it is desirable to include an optical emission filter (not shown in FIG. 1) between the detector 130 and the flow channel. The emission filter preferentially blocks, e.g. by reflection, absorption, scattering, or any other know mechanism, any stray excitation light from the light source that may otherwise impinge on the photosensitive surface of the detector. On the other hand, the emission filter preferentially transmits light emanating from excited particles in the flow channel, which emanating light is typically at longer wavelengths than the excitation light. In some cases, even stray excitation light may be strong enough to overpower the sometimes weak detector signal produced by particle-emanating light. An emission filter is therefore sometimes needed or desired to prevent the detector 130 and/or its amplifier circuit(s) from experiencing saturation, and to allow lower noise detection of the emanating light from the particles. Such an optical filter may of course be incorporated into the analyzer 110 of FIG. 1, and other analyzers disclosed herein. Other techniques can also be used to minimize the amount of excitation light reaching the detector. For example, the excitation light source may be suitably positioned to avoid direct or indirect illumination of the detector by the excitation light beam. Note also that as a result of spatially separating the excitation region(s) from the detection region(s), the optical emission filter, if used, may have more relaxed design requirements than would otherwise be needed due to the spatial separation of excitation region(s) and detection regions(s).

Whichever type of detector 130 is used, the detector generates an output on line 132, which may be supplied to signal processing unit 140. In a simple design, the line 132 may be or comprise a coaxial cable, or a twisted pair of wires. The line 132 carries a time varying output signal, depicted schematically as output 134. The signal processing unit 140 may perform an analysis on the output signal 134. The analysis may include, for example, measuring correlation(s) with one or more other signals, and/or evaluating the frequency content of the output signal. The results of the analysis may be used to provide one or more measures of at least the first particles 105 in the sample, e.g., absolute or relative amounts of such particles in the sample, particle speeds and speed distributions, particle sizes, and so forth. In some cases, the results of the analysis may also be used to provide similar measures of the second particles 106 in the sample. Reference in this regard is made to, e.g., the analyzer of FIG. 12, described below. The signal processing unit 140 may comprise one or more microprocessors and/or microcontrollers, and/or one or more application specific integrated circuits (ASICs), and/or one or more field-programmable gate arrays (FPGAs), and/or any other digital signal processing (DSP) circuitry. The signal processing unit may also optionally include volatile and/or non-volatile memory, storage device(s), and software. Software, hardware, and/or firmware may be tailored to carry out frequency analysis of one or more a time-varying signal, e.g., a set of instructions to carry out a fast Fourier transform (FFT) procedure or other Fourier transform or other transform procedure. In some cases, the signal processing unit may be or comprise a desktop, laptop, notebook, or other portable or non-portable computer system, including e.g. mobile phones, smart phones, or any other type of personal digital assistant, suitably equipped with appropriate interfaces, networks, hardware, and software to carry out the desired signal analysis.

Figure 2:
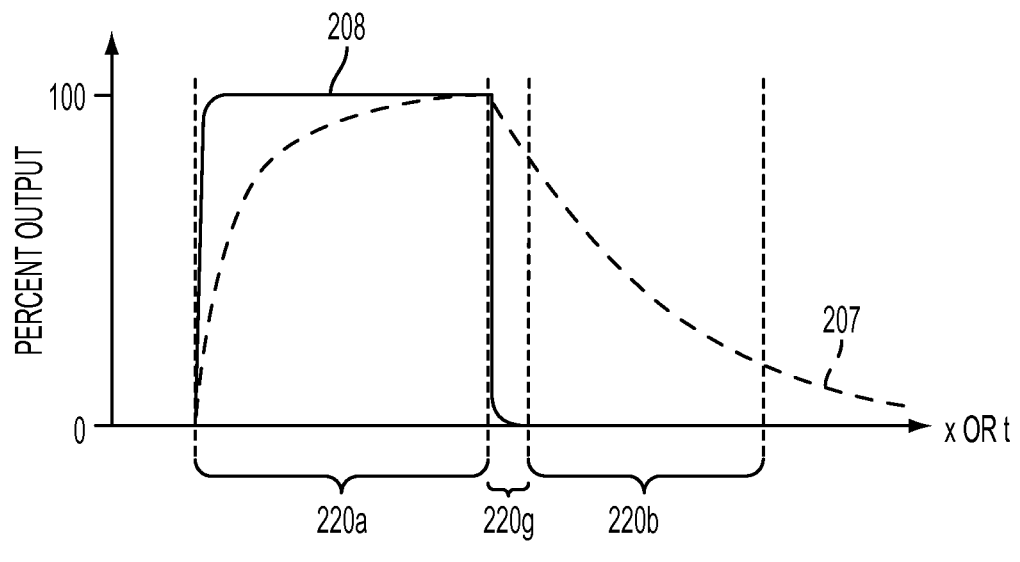
FIG. 2 is a graph of idealized functions of intensity versus time or position for different particle types that may be present in the analyzer of FIG. 1.

Turning now to FIG. 2, we see there a graph of idealized functions of intensity or flux versus time or position for different particle types that may be present in the sample to be analyzed by the analyzer of FIG. 1. The intensity or flux of the emanating light of each particle is shown for simplicity as a percentage of a maximum value. The horizontal axis of the graph may be interpreted as the time measured from a given event, e.g., the time after which a given particle enters the inlet 121a, or it may be interpreted as the position x along the flow direction (x-axis in FIG. 1) of a given particle. Idealized curve 207 is intended to be representative of a given first particle, whose characteristic response time $\tau 1$ for emanating light is relatively long, while idealized curve 208 is intended to be representative of a given second particle, whose characteristic response time $\tau 2$ for emanating light is relatively short. That is, $\tau 2 < \tau 1$. In the graph, regions 220a, 220g, 220b are meant to correspond to the excitation region 120a, the gap region, and the detection zone 120b respectively of the flow channel 123. Inspection of curve 207 shows that as a given first particle 105 travels along the flow channel 123 and enters the excitation region 120a, it becomes excited and the light it emanates in response to the excitation increases to a maximum flux or intensity value. See region 220a of the graph. When such first particle 105 crosses the boundary from the excitation region 120a to the adjacent gap region of the flow channel, the excitation light is removed or substantially reduced. As a result, the amount of light emitted by the first particle (which is still substantially excited) begins to decrease or decay in the region 220g of the graph. When the first particle 105 then crosses the boundary from the gap region to the detection zone 120b of the flow channel 123, excitation light continues to be substantially absent. As a result, the amount of light emitted by the first particle (which is still excited to some extent) continues to decrease or decay in the region 220b of the graph.

Again referring to FIG. 2, inspection of curve 208 shows that as a given second particle 106 travels along the flow channel 123 and enters the excitation region 120a, it also becomes excited, and the light it emanates in response to the excitation also increases to a maximum flux or intensity value. See region 220a of the graph. The light emitted by the second particle may substantially reach its maximum value much faster than that of the first particle, due to the characteristic response time $\tau 2$ being faster than $\tau 1$. When such second particle 106 crosses the boundary from the excitation region 120a to the adjacent gap region of the flow channel, the excitation light is removed or substantially reduced. As a result, the amount of light emitted by the second particle (which is at least initially still substantially excited) begins to decrease or decay in the region 220g of the graph. When the second particle 106 then crosses the boundary from the gap region to the detection zone 120b of the flow channel 123, excitation light continues to be substantially absent. As a result, the amount of light emitted by the second particle (which may still be excited to some extent, or which may no longer be substantially excited) continues to decrease or decay in the region 220b of the graph, or remains at or near zero through the region 220b. As a result of appropriately selecting the longitudinal dimensions of the gap region and the detection zone 120b of the flow channel in view of the characteristic response times $\tau 1$ and $\tau 2$ and in view of the flow speed of the particles, we are able to effectively isolate, from the perspective of the detector, the light emission from the first particle and eliminate the light emission from the second particle in the detection zone 120b.

Figure 3:
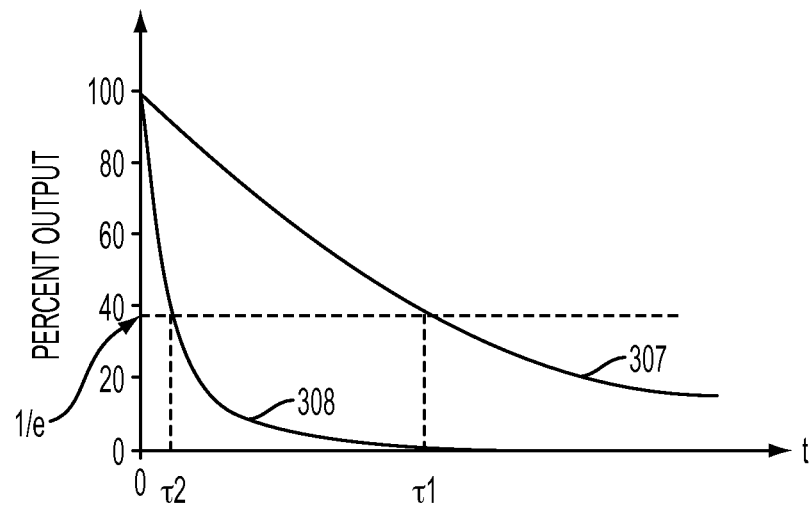
FIG. 3 is a graph of idealized functions having different decay times, to assist the reader's understanding of the disclosed techniques.

FIG. 3 is a graph of idealized functions having different decay times. In the figure, curve 307 exponentially decays from a value of 100% to a value of 1/e (about 36.8%) in a time $\tau 1$. Curve 308 exponentially decays from a value of 100% to the same value of 1/e in a shorter time $\tau 2$. Curve 307 may be representative of light intensity of light emanating from a first excited particle after excitation is removed; curve 308 may be representative of light intensity of light emanating from a second excited particle after excitation is removed.

Figure 4:
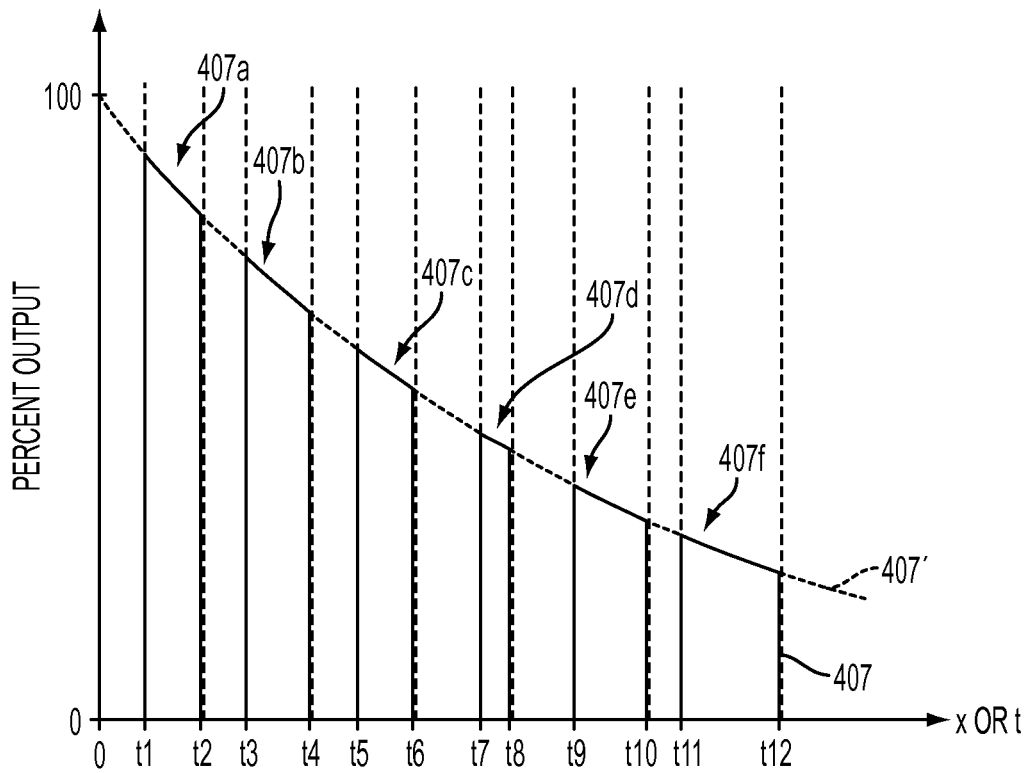
FIG. 4 is a graph of an idealized detector output associated with a detection event of a first particle using an analyzer similar to that of FIG. 1.

The light emanating from an excited particle in the detection zone 120b is alternately transmitted to the detector 130 and (at least partially) blocked from being transmitted to the detector in the detection zone 120b, by virtue of the variable transmission pattern of the spatial filter 126 in combination with the motion of the particle along the flow channel 123. FIG. 4 is a graph of an idealized detector output 407 associated with a detection event of a first particle using an analyzer similar to that of FIG. 1. The vertical axis of the graph represents the detector output. For simplicity, it is shown as a percentage of a maximum value. The horizontal axis of the graph may be interpreted as the time measured from a given event, e.g., the time t1 may be the moment when a given particle exits the gap region and enters the detection zone, or the horizontal axis may be interpreted as the position x along the flow direction (x-axis in FIG. 1) of a given first particle. In the figure, a baseline curve 407' is provided to represent the idealized detector output if the spatial filter were entirely omitted, such that none of the light emanating from the excited particle is blocked from reaching the detector in the detection zone. In the absence of the spatial filter, the baseline curve 407' monotonically decays in the same way that curve 307 (FIG. 3) or curve 207 (FIG. 2) decays. However, when the spatial filter is included, its pattern of alternating transmitting portions and shielding portions (see e.g. elements 126a, 126b respectively in FIG. 1) define corresponding detection regions and shielded regions in the flow channel. In idealized signal 407, the signal portions 407a, 407b, 407c, 407d, 407e, and 407f correspond to five distinct detection regions in the flow channel, and five distinct transmitting portions of the spatial filter. Comparing the width of the signal portions 407a through 407f reveals that the five distinct transmitting portions of the spatial filter do not have the same length in the longitudinal direction, assuming the particle moves at a constant speed through the flow channel. In the areas of signal 407 from time t2 to t3, and from t4 to t5, and from t6 to t7, and from t8 to t9, and from t10 to t11, the detector signal may be at or near a zero level as the result of the blocking action provided by five distinct shielding portions of the spatial filter. Comparing the width of these portions of the signal 407 reveals that the five distinct shielding portions of the spatial filter do not have the same length in the longitudinal direction, again assuming the particle moves at a constant speed through the flow channel.

Of course, the particular idealized signal 407 shown in FIG. 4 is only exemplary and should not be construed to be limiting. For example, the spatial filter may be configured to define more or fewer than six distinct detection regions, and more or fewer than five shielded regions, in the flow channel. The detection regions may all have the same longitudinal dimension, or they may differ from each other. The shielded regions likewise may all have the same longitudinal dimension, or they may differ from each other. The pattern of detection regions and shielded regions defined by the spatial filter may be periodic or non-periodic, as desired.

Figure 5:
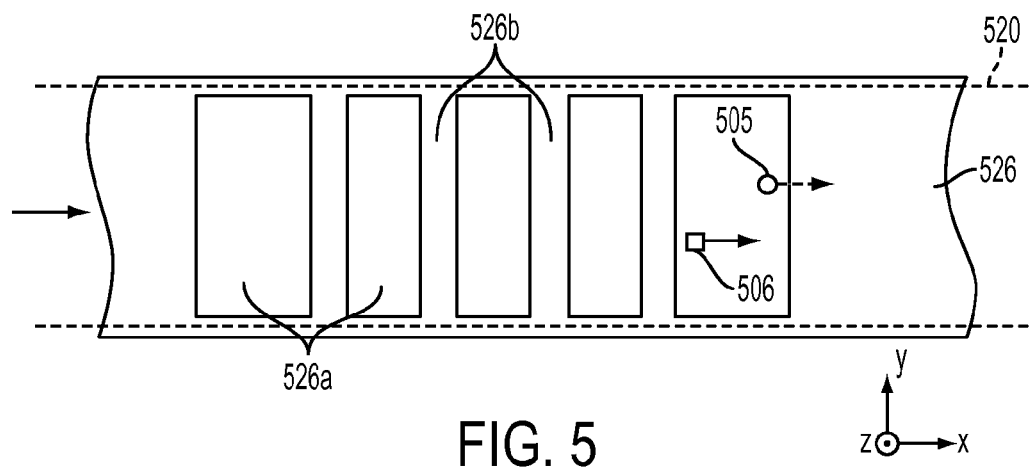
FIG. 5 is a schematic plan or front view of a spatial filter for use in the disclosed analyzers.
Figure 6:
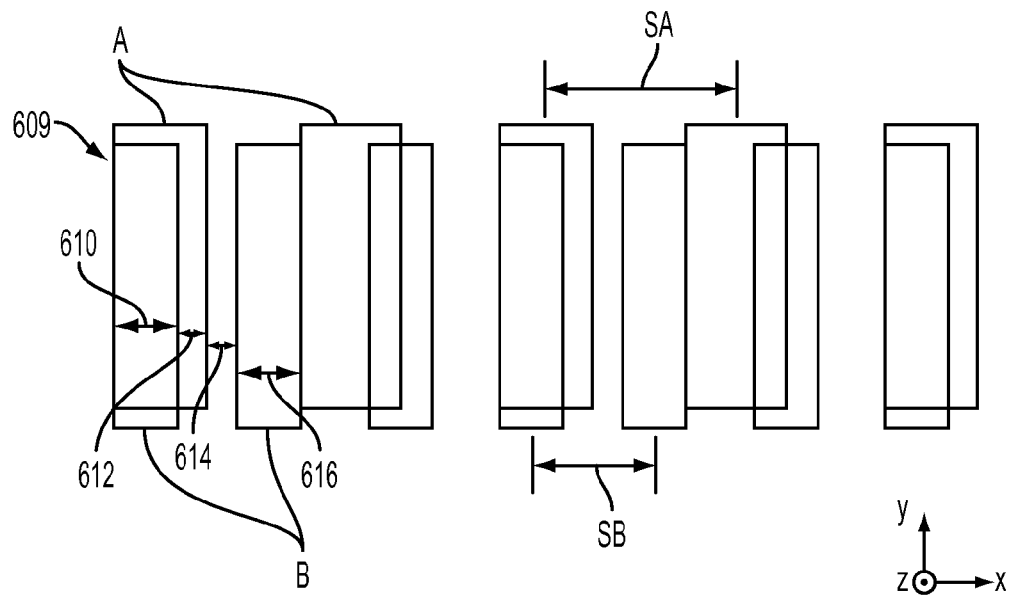
FIG. 6 is a schematic plan or front view of a spatial filter that is or comprises a color mask or filter assembly that is a combination of a first periodic subpattern of spatially separated first transmitting regions and a second periodic subpattern of spatially separated second transmitting regions, the first and second subpatterns being overlapping, and portions of first transmitting regions overlapping with portions of second transmitting regions, where an offset is shown between the first and second subpatterns along the y-direction for ease of explanation.
Figure 7:
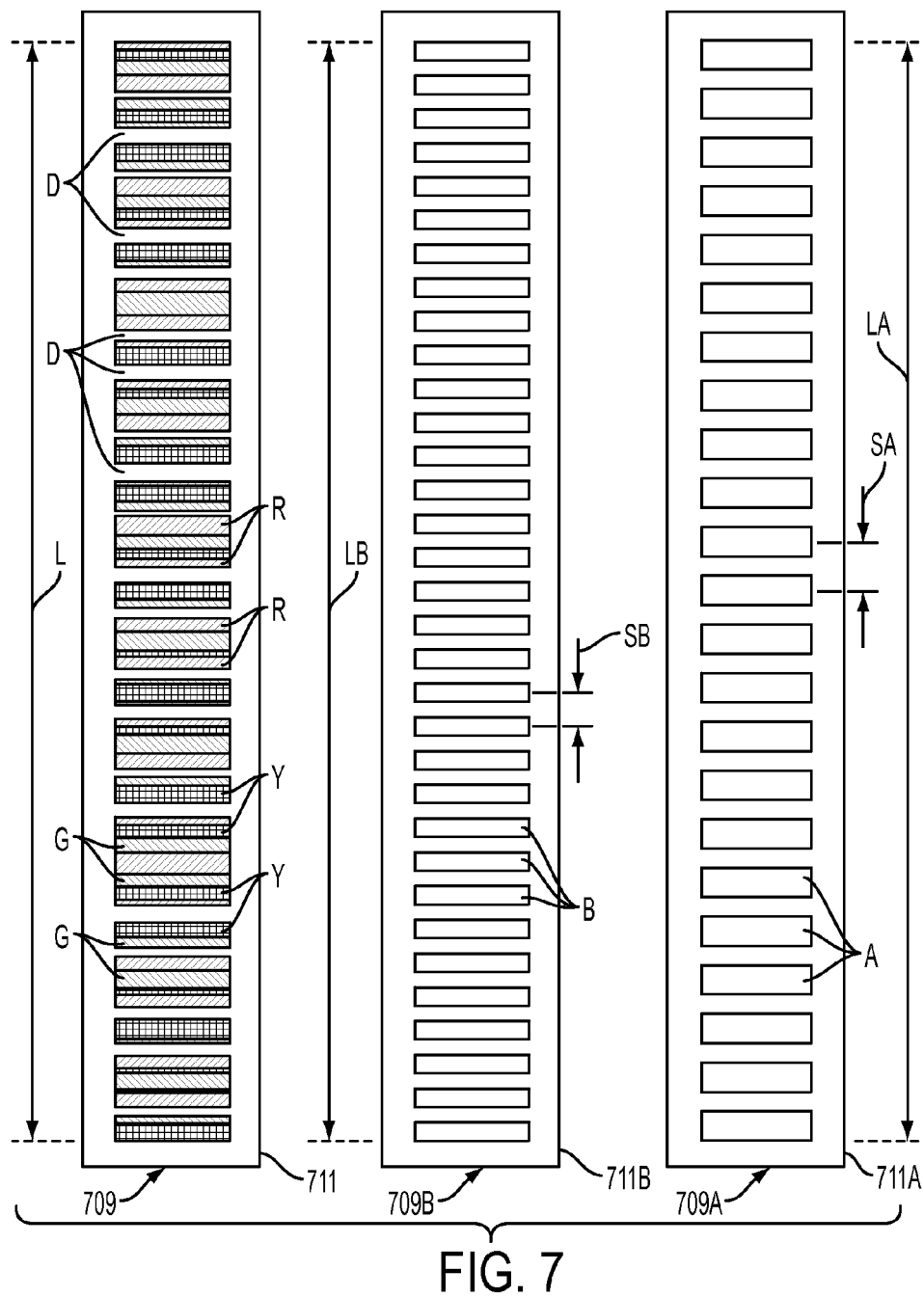
FIG. 7 is a schematic plan or front view of a spatial filter that is or comprises a color mask or filter assembly suitable for use in the disclosed devices, the color mask comprising a combination of a first periodic subpattern of spatially separated first transmitting regions (also shown in the figure) and a second periodic subpattern of spatially separated second transmitting regions (also shown in the figure), the first and second subpatterns being overlapping, and portions of first transmitting regions overlapping with portions of second transmitting regions.

Further considerations regarding possible spatial filter designs are provided in FIGS. 5, 6, and 7. In FIG. 5, we see a schematic plan or front view of a representative spatial filter 526 that may be used in the disclosed analyzers. The spatial filter 526, which may in some cases be a magnified or de-magnified image of a remotely positioned spatial filter as explained below, selectively masks light emanating from particles within the flow channel of a fluid handling device 520. First and second particles 505, 506 are shown to be disposed behind the spatial filter 526, traveling in a flow direction generally parallel to the x-axis. The spatial filter 526 comprises transmitting portions 526a and shielding portions 526b arranged in a pattern of variable transmission along the longitudinal direction. In a simple case, the filter may be an extended film or layer of opaque material in which a number of apertures have been formed. The apertures may correspond to the transmitting portions 526a, and the shielding portions 526b may correspond to the undisturbed opaque material. The longitudinal dimensions (lengths) of the alternating transmitting portions 526a and shielding portions 526b determine the transmission function as a function of position along the x-axis.

The pattern or sequence of transmitting portions 526a and shielding portions 526b in the spatial filter 526 define a transmission function that changes based on longitudinal position, i.e., based on position measured along the x-direction or flow direction. This transmission function may be substantially periodic, or it may instead be substantially non-periodic. An example of a periodic transmission function is a square wave, or a rectangle wave of constant period. A limitation of periodic transmission functions is that they do not typically allow for high spatial resolution of a detected particle. However, this limitation may be unimportant in cases of rare event detection, i.e., in cases where the particle density is low enough so that only a single particle (at most) is likely to be present in the detection portion of the flow channel at any given time. Examples of this may include pathogen detection in water, or rare cell scanning. In this regard, the disclosed analyzers and related techniques are generally well suited for rare event detection. Rare event detection benefits from large throughput and large detection area, but background scatter or autofluorescence typically increases strongly with detection area, hence resulting in the need to reduce such background relative to the signal of interest to achieve acceptable signal-to-noise levels. Another advantage of a periodic transmission function is its ability to produce a clear, strong peak in the frequency spectrum (e.g. the fast Fourier transform, or FFT) of the detector output signal, for a single particle moving at a constant speed in the detection zone.

An example of a non-periodic transmission function is a random function, or a chirped function (having a monotonically increasing or decreasing period). An advantage of non-periodic transmission functions is that they do typically allow for high spatial resolution of a detected particle, by employing correlation techniques to determine the longitudinal position of the particle at a given moment in time. For example, a correlation may be carried out between the time-varying detector output 134 and a signal template representative of the (non-periodic) transmission function. The presence and location of a peak in the correlation can be used to determine the precise position of the particle along the length of the spatial filter 126. This capability is not limited to rare event detection, and can be used with higher particle densities in which multiple particles are present in the detection portion of the flow channel at a given time.

One characteristic of the spatial filter worth noting is its "minimum feature size" ("MFS"). The MFS refers to the length, as measured along the longitudinal direction (i.e., the flow direction, e.g., the x-direction in FIGS. 1 and 5), of the shortest identifiable region of the spatial filter. The shortest identifiable region may in some cases be a transmitting portion, while in other cases it may be a shielding portion, while in still other cases it may be both a transmitting portion and a shielding portion (i.e., if the shortest transmitting portion has the same longitudinal length as the shortest shielding portion, or if all transmitting portions have the same longitudinal length as all shielding portions). The MFS of the spatial filter used in an analyzer has a direct impact on the spatial resolution of the analyzer, with larger MFSs generally corresponding to lower spatial resolutions. Of course, the average or typical particle size also has an impact on spatial resolution. In many cases, it is desirable to design the spatial filter such that the MFS is on the order of the largest average particle size or somewhat greater, e.g., one to two times the average particle size for the largest particle type of interest to be detected.

The spatial filter 526 may be substantially monochromatic, or it may be polychromatic as in the case of a color filter assembly. In a monochromatic spatial filter, the transmitting portions 526a all have substantially the same transmission characteristic, and the shielding portions 526b also all have substantially the same transmission characteristic (but different from that of the transmitting portions). In a simple case, the transmitting portions 526a may all be completely clear, as in the case of an aperture, and the shielding portions 526b may be completely opaque, as in the case of a layer of black ink or other absorptive, reflective, or scattering material. Alternatively, the transmitting portions 526a may all have a given color or filter characteristic, e.g., high transmission for light emanating from excited particles, but low transmission for excitation light. Alternatively, the shielding portions may have a low but non-zero light transmission, as in the case of a grey ink or coating, or a partial absorber or reflector.

In a polychromatic spatial filter, sometimes also referred to herein as a patterned color mask or color filter assembly, at least two different types of transmitting portions 526a are provided: first transmitting portions may have a first transmission characteristic, and second transmitting portions may have a second transmission characteristic, each of these transmission characteristics being different from the (usually opaque or nearly opaque) transmission characteristic of the shielding portions. The first transmission characteristic may correspond to a first filter type, and the second transmission characteristic may correspond to a second filter type. The polychromatic spatial filter may be used in analyzers designed to detect not only a first particle type, which may emit light in a first spectral band, but also a third particle type, which may emit light in a different third spectral band. (In this discussion relating to polychromatic spatial filters, we assume that the first and third particles have relatively long characteristic response times τ1, τ3, in comparison to the second particle type which may emit light having a much shorter characteristic response time τ2. The physical separation of the detection regions from the excitation region(s) may then be used to remove the effect of any excited second particles on the detector output, while allowing both light emanating from first particles, and light emanating from third particles, to produce time-variation in the detector output signal. The different layouts or arrangements of first filter types and second filter types can then be used to ensure that the time variation in the detector output for light emanating from the first particle type is different from the time variation in the detector output for light emanating from the third particle type. A temporal or frequency-based analysis of the time-varying detector output can then distinguish the detection of a first particle from that of a third particle.)

Preferably, the first and second filter types used in the polychromatic filter are tailored to preferentially transmit emanating light from the first and third particle types, respectively. For example, if the first particle emits light predominantly in the red region of the visible spectrum, and the third particle emits light predominantly in the green region of the visible spectrum, first transmitting portions of the polychromatic spatial filter may have a higher transmission for red light than for green light, e.g., they may transmit red light and substantially block green light, and second transmitting portions of the polychromatic spatial filter may have a higher transmission for green light than for red light, e.g., they may transmit green light and substantially block red light. In such cases, the first transmitting portions can be arranged in a periodic fashion with a first spacing or periodicity, and the second transmitting portions can be arranged in a periodic fashion with a different second spacing or periodicity. The different spacings or periodicities provided by the sets of different transmitting portions, together with the fact that the transmission characteristics of these regions are tailored to selectively transmit emanating light from a particular type of particle, can be used to provide two distinct mask frequencies $f_{m1}$, $f_{m2}$ in the frequency spectrum of the detector output signal for the different first and third particles, assuming such particles are traveling at a particular (same) speed.

Further information regarding spatial filters, sometimes referred to as mask arrangements, filter assemblies, color masks, or the like, can be found in U.S. Pat. Nos. 7,701,580 and 8,373,860 and in pending U.S. Publication No. 2011/0222062, the entire disclosures of which are incorporated herein by reference, except to the extent they may directly contradict any of the teachings herein.

In FIG. 6, we see a top view of a color mask or filter assembly 609 that includes a plurality of first filter regions (A) and a plurality of second filter regions (B). The filter assembly 609 may include only 5 first regions (A) and 7 second regions (B), as shown, or it may include more or fewer than 5 first regions and/or more or fewer than 7 second regions, as desired. The first regions (A) are arranged to form a first subpattern of the overall pattern of filter regions, and the second regions (B) are arranged to form a second subpattern. The first filter regions are displaced slightly along the transverse y-axis relative to the second filter regions so that the two different regions can be more clearly identified in the figure, but such transverse displacement may be omitted in practical embodiments. In filter assembly 609, the first subpattern is characterized by a uniform center-to-center spacing SA between neighboring first filter regions (A), and the second subpattern is characterized by a different uniform center-to-center spacing SB between neighboring second filter regions (B). The different spacings provide the subpatterns with different dominant spatial frequencies, which in turn can be used to ensure that the time-varying detector signals associated with different particle types have different temporal frequency content.

The subpatterns in the filter assembly 609 overlap in such a way that at least one first filter region (A) overlaps at least one second filter region (B). The overlap of the filter regions referred to here, however, does not refer to the simple effect that can be observed by physically laying one band pass filter atop a different one. Such physical overlap is a subtractive process, whereas the overlap referred to in FIG. 6 is an additive process. Thus for example, if a band pass filter that transmits only green light is physically laid atop a band pass filter that transmits only red light, the result is typically an opaque region because any red light transmitted by the red filter is blocked by the green filter, and any green light transmitted by the green filter is blocked by the red filter. The filter region overlap of FIG. 6 refers instead to an additive approach, in which the overlap region has a broader range of transmission wavelengths than either of the first and second filter regions individually. Thus, in the context of FIG. 6, if a green filter region overlaps a red filter region, the result is a yellow filter region, which transmits both green light and red light but blocks blue light. In practice, the yellow filter region, with its broader transmission range, would typically be formed by applying a distinct yellow-transmitting material on the overlap region of a transparent substrate, and would not be formed by applying separate layers of a green-transmitting material and a red-transmitting material on the overlap region.

By incorporating additive-type overlap areas rather than subtractive-type overlap areas, a desired spatial periodicity of the first filter regions can be preserved, and the desired spatial periodicity of the second filter regions can also be preserved.

In the filter assembly 609 of FIG. 6, therefore, the overlap of the subpatterns results in four distinct types of light transmitting or blocking areas: area 610, which represents regions of (additive-type) overlap between first filter region (A) and second filter region (B); area 612, which represents the first filter region (A) only; area 614, which represents opaque regions; and area 616, which represents the second filter region (B) only. Each of these areas repeats along the longitudinal direction in accordance with the particular arrangement of first and second filter regions depicted in FIG. 6.

FIG. 7 is a top view of another color mask or filter assembly 709 suitable for use in the disclosed devices, the filter assembly 709 comprising a combination (an additive combination) of a first periodic subpattern 709A of first filter regions A, and a second periodic subpattern 709B of second filter regions B. The filter assembly 709 is similar to filter assembly 609 (FIG. 6) discussed above, insofar as both the subpatterns, and individual filter regions of different types, are overlapping.

The first subpattern 709A, of longitudinal dimension LA, comprises a periodic array of first filter regions A, which are formed as apertures in a generally rectangular opaque region 711A. The first filter regions have a uniform center-to-center spacing of SA. The second subpattern 709B, of longitudinal dimension LB, comprises a periodic array of second filter regions B, which are formed as apertures in a generally rectangular opaque region 711B. The second filter regions have a uniform center-to-center spacing of SB. In the depicted embodiment, SA>SB, and LA=LB=L (the longitudinal dimension of the filter assembly 709).

By properly combining the subpatterns 709A, 709B in an additive fashion, the filter assembly 709 results. Any suitable band pass or transmission characteristics may be used for the first and second filter regions A, B, but for simplicity of description we will assume that the first filter regions (A) transmit green light, and the second filter regions (B) transmit red light. In that case:

- Positions on the filter assembly 709 that correspond to an opaque region on the first subpattern 709A and an opaque region on the second subpattern 709B, provide an opaque region on the filter assembly 709. See regions "D". (See also the generally rectangular opaque region 711.)
- Positions on the filter assembly 709 that correspond to a transmissive region on the first subpattern 709A (filter type A) and an opaque region on the second subpattern 709B, provide a transmissive region that transmits green light (corresponding to filter type A) on the filter assembly 709. See regions "G".
- Positions on the filter assembly 709 that correspond to an opaque region on the first subpattern 709A and a transmissive region on the second subpattern 709B (filter type B), provide a transmissive region that transmits red light (corresponding to filter type B) on the filter assembly 709. See regions "R".
- Positions on the filter assembly 709 that correspond to a transmissive region on the first subpattern 709A (filter type A) and a transmissive region on the second subpattern 709B (filter type B), provide a spectrally broadened transmissive region that transmits yellow light on the filter assembly 709. See regions "Y".

By incorporating the spectrally broadened overlap areas in the filter assembly 709, the uniform spatial periodicity for green light (center-to-center spacing SA) from subpattern 709A, and the different uniform spatial periodicity for red light (center-to-center spacing SB) from subpattern 709B, is preserved. The polychromatic spatial filter or filter assembly 709 can be used in the analyzer of FIG. 1, and other analyzers described herein, to distinguish between first particles, whose emanating light has a long characteristic response time $\tau 1$ and is substantially transmitted by the first filter regions A (and at least partially blocked by the second filter regions B), and third particles, whose emanating light also has a long characteristic response time $\tau 3$ and is substantially transmitted by the second filter regions B (and at least partially blocked by the first filter regions A), while avoiding interfering effects of second particles, whose emanating light has a relatively short characteristic response time $\tau 2$, even in cases where the emanating light from the second particles would be highly transmitted by the first filter regions A and/or the second filter regions B. A detector signal caused by the detection event of the first particle would exhibit a variability having a first dominant frequency (associated with the spacing SA of the first filter regions A), and a detector signal caused by the detection event of the third particle would exhibit a variability having a different third dominant frequency (associated with the spacing SB of the second filter regions B), the third dominant frequency being faster or higher than the first dominant frequency since we assume for this embodiment SB<SA.

In summary, patterned color masks can be utilized in the disclosed analyzers to differentiate signals from objects tagged with long lifetime tags having different spectral emission properties, e.g., different colors or wavelength bands. The tags may also have characteristic response times that are both relatively long but different from each other. The different lifetimes produce different time-varying signal shapes, which can be used by the analyzer as additional differentiation criteria.

Figure 8:
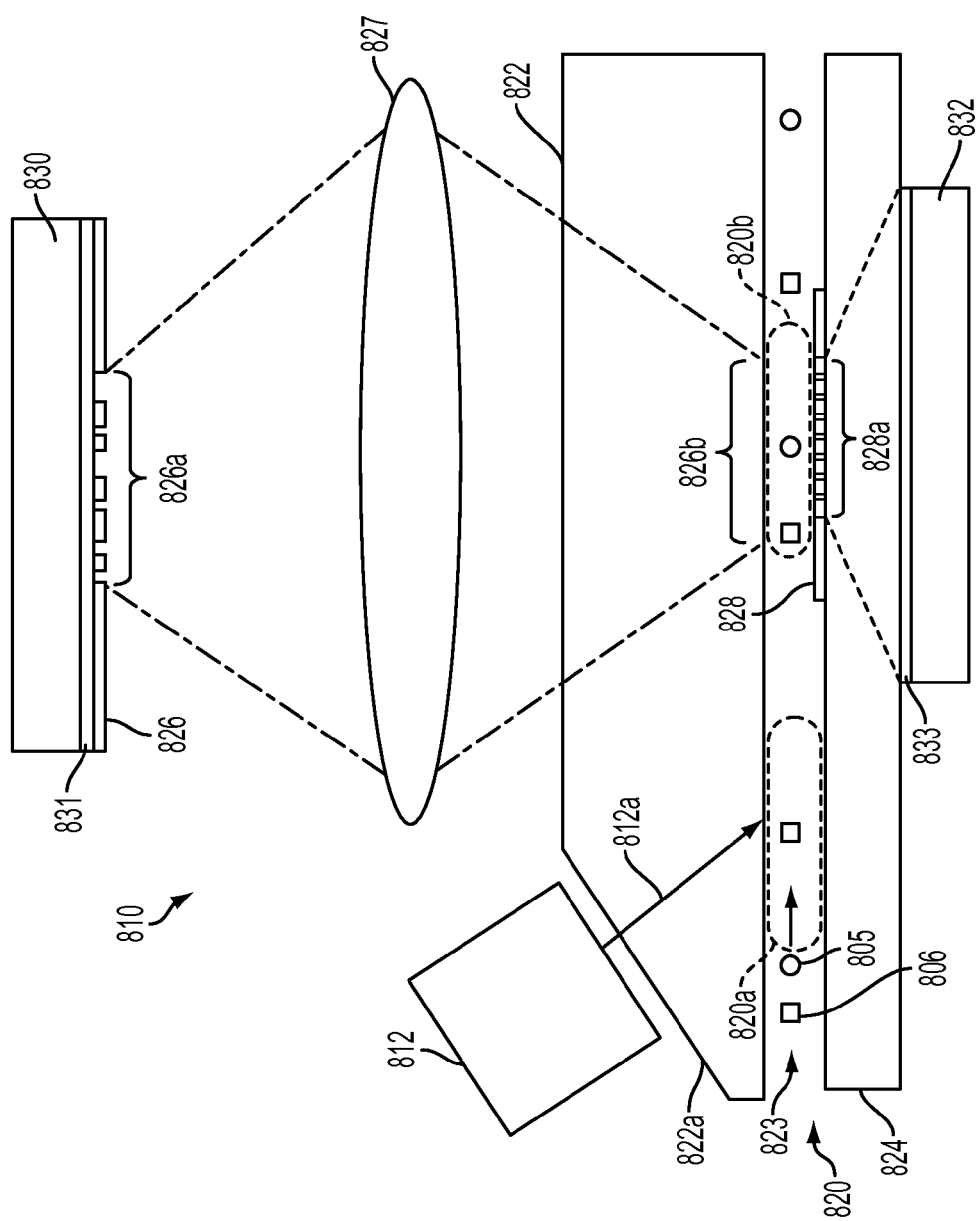
FIG. 8 is a schematic side or sectional view of another sample analyzer that illustrates the use of two independent detector/spatial filter combinations, the analyzer also illustrating both remote sensing and local sensing.

FIG. 8 shows schematically another sample analyzer 810 that illustrates the use of two independent detector/spatial filter combinations, the analyzer 810 also illustrating both remote sensing and local sensing. This analyzer, and the other analyzers described herein, may be or comprise a POC flow cytometer. The analyzer 810 includes a fluidic device 820 which may be a fluidic chip. The fluidic device is adapted to receive the sample of interest to be tested, and to cause the sample to flow through a flow channel 823 formed between confining members 822, 824. A syringe, pump, or other suitable device may be used to provide such sample flow. The sample may include first particles 805 and second particles 806 having different characteristics as discussed elsewhere herein. Light emanating from an excited first particle is assumed to have a characteristic first response time $\tau 1$, and light emanating from an excited second particle is assumed to have a characteristic second response time $\tau 2$, with $\tau 2<\tau 1$. A light source 812 is coupled to interface 822a of the confining member 822, the interface being an angled surface of the confining member 822 to allow excitation light from the light source to propagate within the confining member 822 and illuminate a bounded excitation region 820a of the flow channel 823. The light source 812 may emit excitation light 812a that is centered at or peaks at a first wavelength $\lambda 1$, and the confining member 822 is substantially transmissive to at least the wavelength $\lambda 1$. The light source 812 is preferably a solid state device such as a laser diode or LED.

The excitation light 812a is effective to excite light emission from the first particles 805 and from the second particles 806 in the excitation region 820a. One or more lenses, mirrors, apertures, and/or other optical elements may be used to ensure the excitation region is substantially bounded. A gap region separates the excitation region 820a of the flow channel 823 from a detection zone 820b of the flow channel 823. The detection zone is composed of a number of detection regions interspersed with shielded regions as will be described shortly. The gap region is preferably configured to have a longitudinal dimension sufficient to allow light emanating from the second particles 806 to substantially decay to a small or negligible level by the time such second particles enter the detection zone 820b, even if the second particles travel at a maximum operational flow speed smax through the flow channel. The longitudinal dimension of the gap region is also preferably short enough so that light emanating from the first particles 805 remains relatively high at the time such first particles enter the detection zone 820b, even if the first particles travel at a minimum operational flow speed smin through the flow channel. Further, the length of the detection zone 820b is also preferably short enough so that light emanating from the first particles 805 remains relatively high over substantially the entire length of the detection zone 820b, even if the first particles travel at the minimum operational flow speed smin.

At least some of the light emanating from at least the excited first particles is detected by one or both of photosensitive detectors 830, 832. Each of these detectors may have its own spatial filter associated with it in order to derive more information from the excited particles. A first spatial filter 826 is disposed at the detector 830. A working portion 826a of the filter 826, characterized by a sequence of transmitting and shielding portions arranged along the longitudinal direction, is imaged by an optical element 827 such as one or more suitable lenses and/or mirrors onto the detection zone 826b of the flow channel 823. The optical element 827 may provide magnification, in which case the detection zone 826b may be smaller or larger than the working portion 826a. In this configuration, the detector 830 and the spatial filter 826 are both remotely disposed relative to the fluidic device 820. The remote configuration can allow for more convenient repair or replacement of the remotely-located parts, e.g., the detector 830 and/or the spatial filter 826. In some cases, for example, the spatial filter 826 may be removeably mounted to allow for replacement with a different spatial filter having a different pattern of transmitting and shielding portions.

By contrast, the detector 832, and its associated spatial filter 828, are not remotely configured but are instead disposed locally, i.e., at or on the fluidic device 820. This local configuration can allow for a more compact and simpler design than a remote configuration. The spatial filter 828 has a working portion 828a, which is disposed at or on the confining member 824 at an edge or boundary of the flow channel 823. The working portion 828a also corresponds to a second detection zone of the flow channel 823 for purposes of detector 832. For simplicity, we may assume the second detection zone is the same as the detection zone 820b, but this need not be the case in general. The portion 826b and the portion 828a may likewise be of the same or nominally the same size.

Each of the detectors 830, 832 provides its own detector output which varies in time in accordance with at least: the passage of excited particles through the detection zone 820b of the flow channel 823; and the pattern of transmitting and shielding portions of the respective spatial filter. Each of these detector outputs may then be evaluated and analyzed independently of each other using the various signal analysis techniques discussed herein. Optical emission filters 831, 833 may be provided for the respective detectors 830, 832 in order to block at least any residual excitation light that would otherwise fall on the detectors, while transmitting light emanating from at least one of the particle types.

The analyzer 810 may be configured in numerous different ways. In one simple approach, both detector channels may be configured to detect the same first particles in the sample. This may be done for purposes of redundancy, increased signal-to-noise, or for other reasons. In this simple approach, the filters 831, 833 may each transmit emanating light from the first particles and block excitation light, such that the outputs of each detector 830, 832 contain signal contributions from the first particles 805. The spatial filters 826, 828 may each be monochromatic. Other design details of spatial filters 826, 828 may the same, or different. For example, the spatial filters 826, 828 may both have periodic transmission functions, or they may both have non-periodic transmission functions, or one may have a periodic transmission function and the other may have a non-periodic transmission function. Even if the spatial filters 826, 828 have the same type of transmission function, e.g., periodic, the design details may be different— the transmission function of one of the spatial filters may have a relatively short spatial period, while that of the other spatial filter may have a longer spatial period. If the transmission functions of both of the spatial filters are non-periodic, the non-periodic transmission functions may likewise be the same, or very different.

Alternatively, the analyzer 810 may be configured so that one detector channel, e.g. the detector 830/spatial filter 826 combination, detects the first particles, while the other detector channel, e.g. the detector 832/spatial filter 828 combination, detects third particles, where the third particles have an associated characteristic response time $\tau 3$ of roughly the same order as $\tau 1$, or at least where $\tau 2 < \tau 3$, and where light emanating from the third particles can be spectrally separated (at least in part) from the light emanating from the first particles using one or more suitable optical filters. In this case, the spatial separation of the detection zone 820b from the excitation region 820a is effective to suppress detection of the second particles, or to suppress interference from light emanating from the second particles. Then, in order to separate detection of first particles from the detection of third particles, optical filtering may be employed. For example, filter 831 may block light emanating from the third particles and block excitation light, but transmit light emanating from the first particles 805, while the filter 833 may block light emanating from the first particles 805 and block excitation light, but transmit light emanating from the third particles. The spatial filters 826, 828 may each be monochromatic, and other design details of the spatial filters may the same, or different. For example, as discussed above, the spatial filters 826, 828 may both have periodic transmission functions, or they may both have non-periodic transmission functions, or one may have a periodic transmission function and the other may have a non-periodic transmission function.

In still another approach, the analyzer 810 may be configured so that one or both of the detector channels detects at least two different particle types. For example, the detector channel comprising the detector 830/spatial filter 826 combination may be configured to detect both first particles and third particles, where again the third particles are assumed to have an associated characteristic response time $\tau 3$ of roughly the same order as $\tau$, or at least where $\tau 2 < \tau 3$, and where light emanating from the third particles can be spectrally separated (at least in part) from the light emanating from the first particles using one or more suitable optical filters. In this case, spatial filter 826 may be or comprise a polychromatic spatial filter such as those described in connection with FIGS. 6 and 7. The different filter types used in such spatial filter 826 may then be chosen to selectively transmit light emanating from first particles and light emanating from third particles, such different filter types being arranged such that the spatial filter 826 effectively provides different transmission functions for light emanating from the first particles compared to light emanating from the third particles. (Note that the emission filter 831, if included, preferably transmits light emanating from first particles and light emanating from third particles, but blocks excitation light.) The different transmission functions may have different spatial frequencies, which produce different temporal frequencies in the time-varying detector output depending on whether an excited first particle or an excited third particle is traveling through the detection zone of the flow channel 823 at a given speed. Still with respect to this approach, the other detector channel, e.g., the detector channel comprising the detector 832/spatial filter 828 combination, may be configured to detect: the first particles only, or the third particles only, or both the first particles and the third particles, or a different type of particle only (e.g. a fourth type of particle only, where fourth particles are assumed to have an associated characteristic response time $\tau 4$ of roughly the same order as $\tau 1$ and/or $\tau 3$, or at least where $\tau 2 < \tau 4$, and where light emanating from the fourth particles may be spectrally separated (at least in part) from the light emanating from the first and third particles using one or more suitable optical filters), or other combinations of particle types. Depending on the types of particles to be detected by the detector 832/spatial filter 828 combination, the spatial filter 828 may be monochromatic or polychromatic, and it may be periodic or non-periodic as desired.

In some cases, one or more excitation light sources may be provided in addition to light source 812. For example, if one or more of the particles to be detected are not substantially excited by the light emitted by the source 812, another light source, whose wavelength and/or other output characteristics are suitable to excite the additional particle(s) to be detected), may be added. The additional light source may be configured to illuminate the same excitation region 820a, or one or more different excitation region(s) of the flow channel 823.

In some cases, one of the particle types to be detected may have a substantially different characteristic response time compared to another particle type to be detected. For example, if a first and third particle type are to be detected, and a second particle type is to be suppressed (and not of interest), the characteristic response times of the first, second, and third particle types may satisfy the condition $\tau 2 \ll \tau 3 \ll \tau 1$. In that case, a first detector channel may be configured to measure the first particles, and a second detector channel may be configured to measure the third particles. The spatial filter and detector for the first detector channel preferably defines a detection zone that is substantially longer in the longitudinal direction, to accommodate the longer response time $\tau 1$, than the detection zone for the second detector channel, which is sized to accommodate the shorter response time $\tau 3$.

Furthermore, a variety of configurations for the detectors and the spatial filters are also contemplated. For example, analyzer 810 may be modified to provide: a remote detector 832 but a local spatial filter 828; a remote detector 832 and a remote spatial filter 828; a remote detector 830 but a local spatial filter 826; and a local detector 830 and a local spatial filter 826. In some cases, the spatial filter 826 may have substantially the same arrangement or pattern of transmitting and shielding portions as spatial filter 828. In other cases, the patterns for these filters may be different. One spatial filter may have a periodic pattern, while the other spatial filter may have a non-periodic pattern. Alternatively, one spatial filter may have a first periodic pattern, and the other spatial filter may have a second periodic pattern different from the first pattern. Alternatively, one spatial filter may have a first non-periodic pattern, and the other spatial filter may have a second non-periodic pattern different from the first pattern. One spatial filter may have a monochromatic pattern, while the other spatial filter may have a polychromatic pattern. Alternatively, both spatial filters may have monochromatic patterns, or both may have polychromatic patterns. Furthermore, the detectors 830, 832 may have substantially the same detector characteristics, or they may be different. For example, the detectors 830, 832 may both be silicon photodiodes, or they may be photodiodes made of some other detector material, and they may thus have substantially the same spectral responsivity. Alternatively, the detectors 830, 832 may be composed of different detector materials (e.g., different semiconductors), and they may thus have substantially different spectral responsivities.

In an exemplary embodiment, the analyzer 810 may be made in a relatively small format suitable for use in POC applications. In such embodiment, the thicknesses of elements 822, 823, and 824 in FIG. 13 may be 2 mm, 25 microns, and 75 to 100 microns, respectively, but these dimensions should not be construed to be limiting. Other details regarding suitable analyzer features may be found in Patent Application Publication US 2010/0201988 (Kiesel et al.).

The reader will understand that the concept shown in FIG. 8 of using two different detector/spatial filter combinations can be extended in a straightforward fashion to more than two such combinations. For example, three, four, or more different detectors and/or detector/spatial filter combinations may be used for a given flow channel and analyzer. Furthermore, two, three, or more laser diodes or other excitation sources may be arranged to illuminate substantially the same excitation region 820a, or to illuminate different excitation regions, for example, by arranging such sources in a ring geometry. Such concepts can also be applied to the other analyzers disclosed herein.

Figure 9:
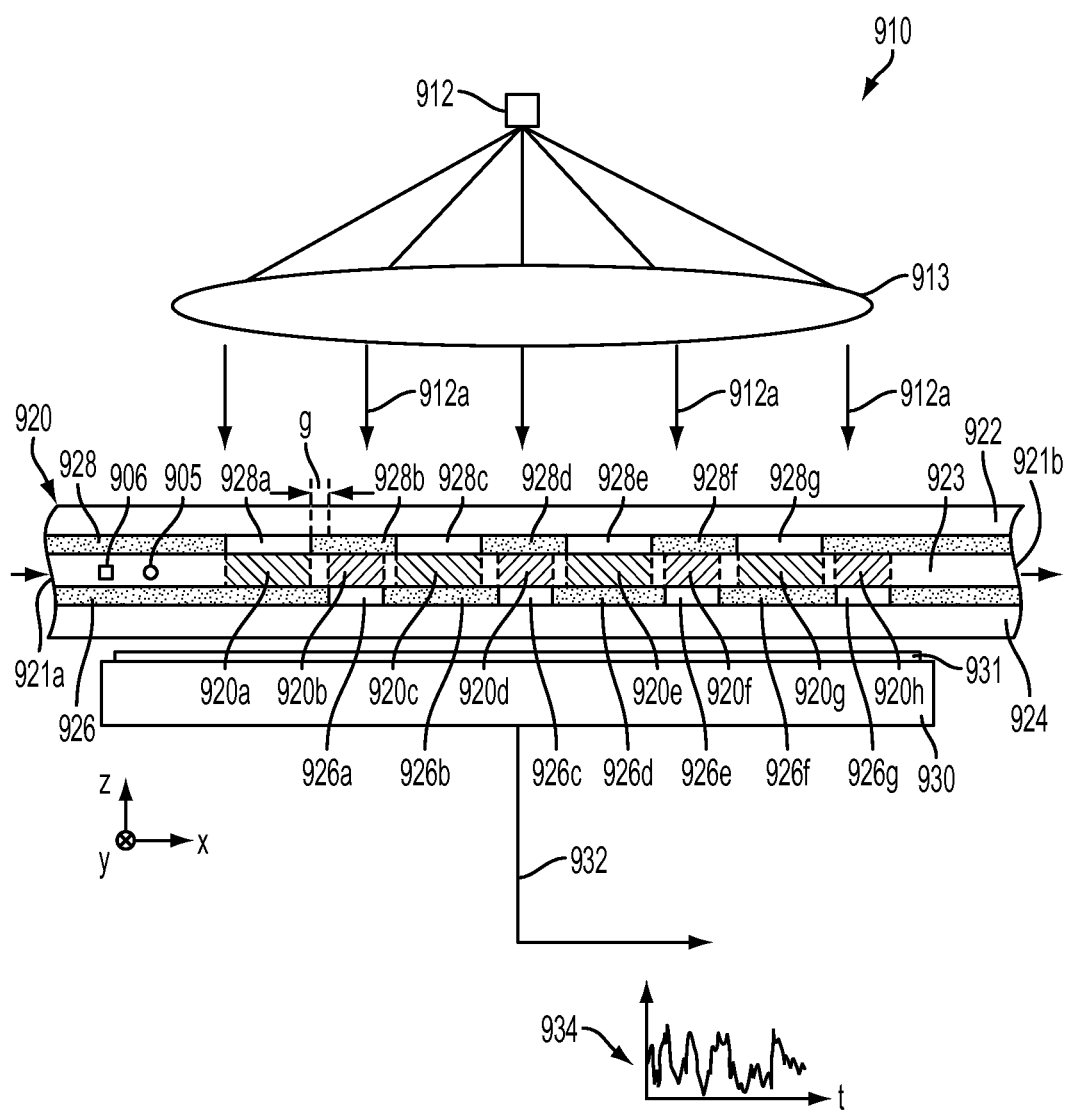
FIG. 9 is a schematic side or sectional view of another sample analyzer, illustrating repetitive, interspersed excitation and detection.

Turning now to FIG. 9, we see there a schematic view of another sample analyzer 910. Unlike the analyzer 110 of FIG. 1 or the analyzer 810 of FIG. 8, the analyzer 910 utilizes repetitive, interspersed excitation and detection regions. However, the reader is cautioned that features discussed in connection with any of the embodiments herein should be understood as also applying (at least as optional features or modifications) to all other disclosed embodiments, unless otherwise indicated.

The analyzer 910 therefore incorporates a light source 912, a fluid handling device 920, a first spatial filter 926, and a detector 930. The analyzer 910 also includes a second spatial filter 928, which is used in combination with the light source 912 so as to define a plurality of distinct excitation regions of the flow channel, just as the first spatial filter 926 is used in combination with the detector 930 to define a plurality of distinct detection regions of the flow channel. The fluidic device 920 is adapted to receive a sample of interest to be analyzed. The sample may enter the device 920 at an inlet 921a thereof and exit the device 920 at an outlet 921b thereof, flowing generally along the x-direction through a flow channel 923 formed between confining members 922, 924. The members 922, 924 may be the same as or similar to other confining members discussed herein.

The light source 912 may be the same as or similar to other excitation light sources discussed herein. The light source 912 thus preferably emits excitation light in a light beam 912a towards the fluidic device 920. To facilitate this, an optical element 913 such as one or more suitable lenses and/or mirrors may be used with or included in the light source. The excitation light 912a may comprise light of a first wavelength $\lambda 1$, and in some cases, the excitation light may have a peak output at the wavelength $\lambda 1$. The spectral makeup or composition of the excitation light emitted by the source 912 is preferably tailored to excite at least particles of a first type that may be present in the sample.

The confining member 922 transmits the light beam 912a such that it illuminates the sample disposed within the flow channel 923. However, the second spatial filter 928 is interposed between the light source 912 and the flow channel 923, and its pattern of variable transmission operates to allow the light beam 912a to illuminate only selected portions, referred to as excitation regions, of the flow channel 923. The spatial filter 928 is depicted as having transmitting portions 928a, 928c, 928e, and 928g arranged in alternating fashion with shielding portions 928b, 928d, 928f. Other numbers of transmitting portions and shielding portions are of course also contemplated. The second spatial filter may be the same as or similar to other spatial filters discussed herein; thus, the second spatial filter may be monochromatic or polychromatic, it may be mounted in a remote or local configuration, its transmission function may be periodic or non-periodic, and it may have a desired minimum feature size MFS. In a simple case, the transmitting portions 928a, 928c, 928e, and 928g may all be completely clear, as in the case of apertures, and the shielding portions 928b, 928d, and 928f may be completely opaque, as in the case of a layer of black ink or other absorptive, reflective, or scattering material. Light from the light beam 912a passes through the transmitting portions of the second spatial filter to define distinct, spatially separated excitation regions 920a, 920c, 920e, and 920g of the flow channel 923 as shown in the figure, with remaining regions of the flow channel preferably remaining substantially non-illuminated with the excitation light.

In some cases the second spatial filter 928 may be omitted and replaced with one or more suitable optical elements that achieve the same result of spatially separated excitation regions 920a, 920c, 920e, and 920g. For example, a refractive or diffractive focusing optic may be designed to concentrate light from a source into the excitation regions while avoiding other portions of the flow channel. Alternatively, an array of small individual light sources may be configured to illuminate the excitation regions while avoiding other portions of the flow channel.

The sample is depicted as containing two types of particles: first particles 905, and second particles 906. The first particles 905 are assumed to be particles whose presence in the sample is sought to be detected and quantified by the analyzer 910, while the second particles 906 are assumed to be particles or any other component of the sample that, in the case of FIG. 9, is not of interest, the presence of which is not sought to be detected or quantified by the analyzer 910. We assume that both the first particles 905 and the second particles 906 are excited by the excitation light 912a, such that they emanate light, such emanating light typically propagating in all directions. In conventional analyzers, the light emitted by the second particles 906 might ordinarily interfere with the detection of light emitted by the first particles 905. The light emitted by the second particles might for example constitute relatively strong autofluorescence arising from particles or any other component of the sample, while the light emitted by the first particles might constitute a weaker fluorescent emission from particles such as cells that are tagged with a particular fluorescent dye. Light emitted by the second particles may also be or comprise autofluorescence from a "complex" carrier medium. The autofluorescence from such medium may be relatively weak per unit area or volume, but if relatively large excitation region(s) and/or detection regions are used, the overall area or volume that emits such weak autofluorescence may be much larger than the area of the tagged particle of interest.

Consistent with our earlier discussion, we assume that light emitted by the first particles has a characteristic first response time $\tau 1$, and that light emitted by the second particles has a characteristic second response time $\tau 2$, and that the first response time is greater than (i.e., longer than, or slower than) the second response time: $\tau 1 > \tau 2$. In some cases, the light emanating from the different particle types may differ from each other in other ways also, such as in their spectral characteristics.

Keeping in mind that the sample is pumped or otherwise drawn through the flow channel 923 from the inlet 921a to the outlet 921b, particles in the sample will alternately pass through excitation regions and regions of the flow channel that are not illuminated with excitation light. As a given particle passes through a given excitation region, the particle becomes increasingly excited and gives off an increasing amount of emanating light. (Stated differently, as the given particle passes through the excitation region, more fluorescence tags attached to the particle may become excited. The excitation probability may depend on excitation flux and absorption cross section of the particles. Each tag may become excited multiple times and emit multiple photons during one pass through the excitation region. Each particle may be tagged with a multitude of fluorophores. For example, an individual CD4 cell may be tagged with 40 thousand fluorophores, and an individual Giardia cell may be tagged with a few hundred thousand fluorophores.) But when such particle exits the excitation region, the excitation decays, and the amount of emanating light also decays. This growth and decay in emanating light is made to repeat by providing the multiple transmitting portions in the spatial filter 928, corresponding to the multiple excitation regions of the flow channel.

The analyzer also includes a detection channel comprising the combination of detector 930 and first spatial filter 926. An emission filter 931 may also be provided as shown to block extraneous excitation light, and/or other undesired light, and transmit light emanating from particles of interest. The spatial filter 926 comprises transmitting portions 926a, 926c, 926e, and 926g arranged in alternating fashion with shielding portions 926b, 926d, and 926f as shown in the figure. Other numbers of transmitting portions and shielding portions are of course also contemplated. The first spatial filter may be the same as or similar to other spatial filters discussed herein; thus, it may be monochromatic or polychromatic, it may be mounted in a remote or local configuration, its transmission function may be periodic or non-periodic, and it may have a desired minimum feature size MFS. In a simple case, the transmitting portions 926a, 926c, 926e, and 926g may all be completely clear, as in the case of apertures, and the shielding portions 926b, 926d, and 926f may be completely opaque, as in the case of a layer of black ink or other absorptive, reflective, or scattering material. The transmitting portions of the first spatial filter in combination with the placement of the detector 930 define a plurality of distinct, spatially separated detection regions 920b, 920d, 920f, and 920h in the flow channel 923: light emitted by an excited particle located in any of the detection regions passes through the corresponding transmitting portion of the first spatial filter and impinges on the active area of the photosensitive detector, producing an output signal on line 932. On the other hand, light emitted by an excited particle located in any other portion of the flow channel 923 may be substantially blocked from reaching the detector 930 by the shielding portions of first spatial filter 926. The detector 930 may be the same as or similar to other photosensitive detectors discussed herein.

In the analyzer 910, the first and second spatial filters are arranged and configured with respect to each other so that the excitation regions 920a, 920c, 920e, 920g are interspersed with the detection regions 920b, 920d, 920f, and 920h. Furthermore, the excitation regions 920a, 920c, 920e, 920g are all substantially fully shielded from the detector 930 by the first spatial filter 926. With this arrangement, the detector 930 is responsive only to excited particles whose emanating light is decaying in strength due to the substantial absence of excitation light in the detection regions.

Preferably, the first and second spatial filters are further arranged and configured with respect to each other to define a gap region at least between each excitation region and a neighboring downstream detection region. Thus, with reference to FIG. 9, a gap region is preferably provided between excitation region 920a and detection region 920b, and between excitation region 920c and detection region 920d, and between excitation region 920e and detection region 920f, and between excitation region 920g and detection region 920h. Each gap region may be considered to extend from the downstream boundary of a given excitation region to an upstream boundary of the nearest downstream detection region. These gap regions may be substantially identical in size and shape (and longitudinal length), or they may be somewhat different from each other. Preferably, each of these gap regions has a longitudinal dimension "g" (see FIG. 9) that is long enough so that light emanating from a given second particle has decreased to a negligible intensity or flux, even at the fastest operational flow speed (smax), at the moment such second particle enters a given detection region. This condition may be expressed as g>τ2*smax. Thus, for example, the fluorescence from even a fast-moving unwanted component may have an intensity, when entering the detection area, of less than 37% of its initial intensity; desirably, g>2*τ2*smax, so that such intensity would be less than 14% of its initial intensity, or more desirably, g>4.5*τ2*smax, so that such intensity would be less than 1% of its initial intensity. However, the dimension g of each of the gap regions is also preferably short enough so that light emanating from a given first particle has an intensity or flux that is relatively high, even at the slowest operational flow speed (smin), at the moment such first particle enters a given detection region. This condition may be expressed as g<τ1*smin. Thus, for example, the tag fluorescence for a slow-moving particle of interest may have an intensity, when entering the detection area, of greater than 37% of its initial intensity; desirably, g<0.5*τ1*smin, so that such intensity would be greater than 61% of its initial intensity, or more desirably, g is even less, so that such intensity would be close to 100% of its initial intensity. Moreover, each detection region preferably has a longitudinal dimension or length that is short enough so that light emanating from a given first particle is relatively high (e.g. is maintained above a minimum threshold level), even at the slowest operation flow speed (smin), throughout the time that such particle is present in such detection region. This latter condition may be expressed as Lmax<2*τ1*smin, where Lmax represents the maximum length of any of the individual detection regions. (In cases where the detection regions all have the same longitudinal length, then Lmax represents the length of each detection region.) Thus, for example, the tag fluorescence for a slow-moving particle of interest may have an intensity, when exiting the longest detection region, greater than about 14% (or, for example, greater than about 10%) of its initial intensity when it entered such detection region; desirably, such intensity would be substantially greater than 10% or 14% of its initial intensity, e.g., in a range of 30-50% or more.

Comparing the analyzer design of FIG. 9 with that of FIG. 1 or 8, we see that by employing repetitive, interspersed excitation and detection regions (such as in the embodiment of FIG. 9), we can accommodate slower flow speeds, faster (shorter) characteristic response times τ1, and/or a longer overall detection zone (or longer overall spatial filter) than can be accommodated using a single unitary excitation region. This is because in the design of FIG. 9, the emanating light from a given first particle only needs to remain at measurable levels (e.g. above a minimum threshold level) over the longitudinal span of one detection region, rather than over the longitudinal span of the detection zone which encompasses the entire set of detection regions. Thus, because of the interspersed excitation and detection, the relationship between L1 (the length along the flow channel of the collective set of all detection regions defined by the first spatial filter) and τ1 is no longer important. For example, L1 need not be less than 2*τ1*smin.

However, like the analyzers of FIGS. 1 and 8, the analyzer 910 also produces a time-varying detector output resulting from excited particles of the first particle type rather than from excited particles of the second particle type. As an excited first particle 905 passes through the flow channel 923, it passes through multiple spatially separated detection regions, in which emanating light is transmitted through a given one of the transmitting portions of the first spatial filter 926 to the detector 930, and it passes through shielded regions, in which emanating light is at least partially blocked from the detector 930 by a given one of the shielding portions of the first spatial filter 926. The alternating transmitting and blocking of the emanating light produces a time variation in the detector output 932. (In contrast, an excited second particle 906 does not substantially contribute to the detector output or its time variation because when the second particle 906 is located in any given detection region, its emanating light has decayed to negligible levels by virtue of the sufficient time delay produced by the gap between the given detection region and the nearest upstream excitation region.) An exemplary (idealized) time-varying output signal 934 is shown in FIG. 9. A signal processing unit, as discussed elsewhere herein, can be used to evaluate the detector output signal, and provide a measure of at least the first particles in the sample based on the evaluation.

Figure 10:
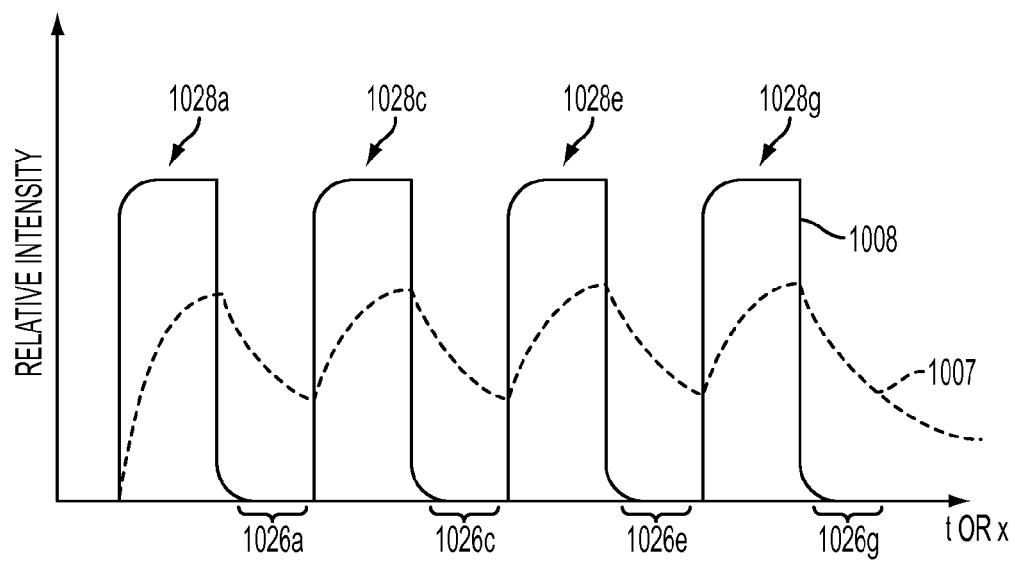
FIG. 10 is a graph of idealized functions of intensity versus time or position for different particle types that may be present in the analyzer of FIG. 9.

Turning now to FIG. 10, we see there a graph of idealized functions of intensity or flux versus time or position for different particle types that may be present in the sample to be analyzed by the analyzer of FIG. 9. The intensity or flux of the emanating light of each particle is provided along the vertical axis of the graph as a relative intensity. The horizontal axis of the graph may be interpreted as the time measured from a given event, e.g., the time after which a given particle enters the inlet 921a, or it may be interpreted as the position x along the flow direction (x-axis in FIG. 9) of a given particle. Idealized curve 1007 is intended to be representative of a given first particle, whose characteristic response time τ1 for emanating light is relatively long, while idealized curve 1008 is intended to be representative of a given second particle, whose characteristic response time τ2 for emanating light is relatively short. That is, τ2<τ1. In the graph, the roughly rectangular-shaped features 1028a, 1020c, 1028e, 1028g are meant to correspond to the excitation regions 920a, 920c, 920e, 920g, respectively, and the regions 1026a, 1026c, 1026e, 1026g are meant to correspond to the detection regions 920b, 920d, 920f, 920h respectively of the flow channel 923. Note that features or regions corresponding to the gap regions of the flow channel 923 are not specifically identified by reference number in FIG. 10. Inspection of curve 1007 shows that as a given first particle 905 travels along the flow channel 923 and enters the initial excitation region 920a, it becomes excited and the light it emanates in response to the excitation increases to a relative maximum flux or intensity value. When such first particle 905 crosses the boundary from the excitation region 920a to the adjacent gap region of the flow channel, the excitation light is removed or substantially reduced. As a result, the amount of light emitted by the first particle (which is still substantially excited) begins to decrease or decay. When the first particle 905 then crosses the boundary from the gap region to the detection region 920b of the flow channel 923, excitation light continues to be substantially absent. As a result, the amount of light emitted by the first particle (which is still excited to some extent) continues to decrease or decay in the region 1026a of the graph. Thereafter, the excitation level and the flux or intensity level of emanating light of first particle rises and falls in the triple sequence provided by excitation regions 920c, 920e, 920g interspersed with gap regions and detection regions 920d, 920f, 920h.

Again referring to FIG. 10, inspection of curve 1008 shows that as a given second particle 906 travels along the flow channel 923 and enters the initial excitation region 920a, it also becomes excited, and the light it emanates in response to the excitation also increases to a relative maximum flux or intensity value. See feature 1028a of the graph. The light emitted by the second particle may substantially reach its maximum value much faster than that of the first particle. When such second particle 906 crosses the boundary from the excitation region 920a to the adjacent gap region of the flow channel, the excitation light is removed or substantially reduced. As a result, the amount of light emitted by the second particle (which is at least initially still substantially excited) begins to decrease or decay. When the second particle 906 then crosses the boundary from the gap region to the initial detection region 920b of the flow channel 923, excitation light continues to be substantially absent. As a result, the amount of light emitted by the second particle (which may still be excited to some extent, or which may no longer be substantially excited) continues to decrease or decay in the region 1026a of the graph, or remains at or near zero through the region 1026a. As a result of appropriately selecting the longitudinal dimensions of the gap region and the detection region 920b of the flow channel in view of the characteristic response times $\tau 1$ and $\tau 2$ and in view of the flow speed of the particles, we are able to effectively isolate, from the perspective of the detector, the light emission from the first particle and eliminate the light emission from the second particle in the detection region 920b. Thereafter, the excitation level and the flux or intensity level of emanating light of second particle rises and falls in the triple sequence provided by excitation regions 920c, 920e, 920g interspersed with gap regions and detection regions 920d, 920f, 920h, and the light emission from the second particle is preferably small or substantially zero throughout the regions 1026a, 1026c, 1026e, 1026g of the graph due to the presence of gap regions in the flow channel 923.

Figure 11:
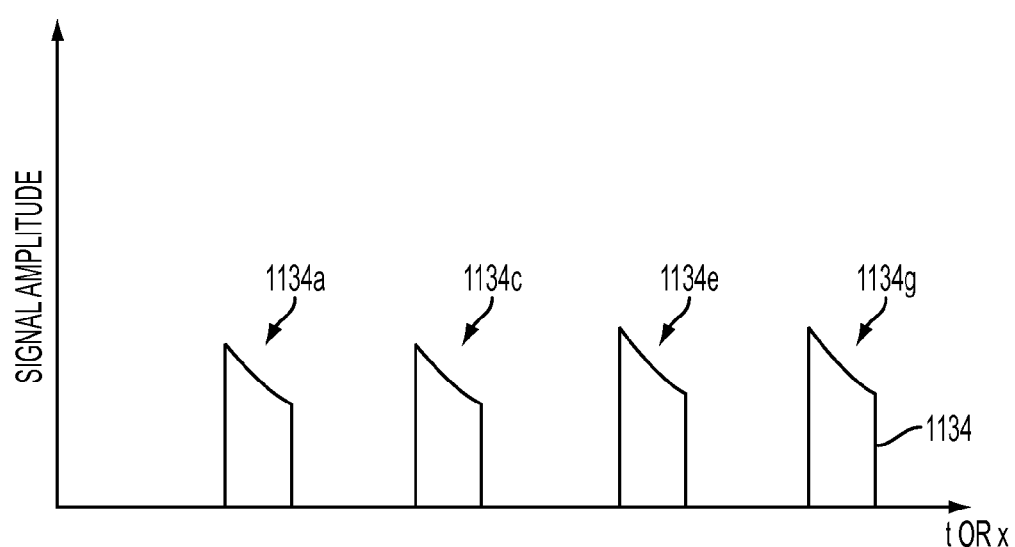
FIG. 11 is a graph of an idealized detector output associated with a detection event of a first particle using an analyzer similar to that of FIG. 9.

Only some of the emanating light represented in FIG. 10 is sensed by the detector 930, due to the selective shielding effect of the first spatial filter 926. In particular, only emanating light occurring in regions 1026a, 1026c, 1026e, 1026g of FIG. 10, which regions correspond respectively to the transmitting portions 926a, 926c, 926e, 926g of the spatial filter 926 and which correspond respectively to the detection regions 920b, 920d, 920f, 920h of the flow channel 923, is sensed by the detector 930. The result is an idealized detector output signal 1134 depicted schematically in FIG. 11. The idealized signal 1134 is associated with a detection event of a first particle using an analyzer similar to that of FIG. 9, and the signal 1134 is substantially insensitive to the presence of particles of the second particle type in the sample. The vertical axis of the graph of FIG. 11 represents the detector output in arbitrary units. The horizontal axis of the graph may be substantially the same as that of FIG. 10. Inspection of the signal 1134 reveals that it is substantially zero except at times (or positions) corresponding to regions 1026a, 1026c, 1026e, 1026g of FIG. 10, during which the signal substantially tracks the intensity of flux of the first particle as it decays with time. Such nonzero portions of the detector signal are identified as signal portions 1134a, 1134c, 1134e, and 1134g, respectively, which are seen to have the same or similar widths along the horizontal axis. The widths of these signal portions reveal that the four distinct transmitting portions of the spatial filter 926 have the same or similar lengths in the longitudinal direction, assuming the first particle responsible for signal 1134 moves at a constant speed through the flow channel. In the areas of signal 1134 between the signal portions 1134a, 1134c, 1134e, and 1134g, the detector signal may be at or near a zero level as the result of the blocking action provided by the three distinct shielding portions 926b, 926d, 926f of the spatial filter. Comparing the width of these portions of the signal 1134 reveals that the three distinct shielding portions of the spatial filter have the same or similar lengths in the longitudinal direction, again assuming the particle moves at a constant speed through the flow channel.

Of course, the particular idealized signal 1134 shown in FIG. 11 is only exemplary and should not be construed to be limiting. For example, the spatial filter may be configured to define more or fewer than four distinct detection regions, and more or fewer than three shielded regions, in the flow channel. The detection regions may all have the same longitudinal dimension, or they may differ from each other. The shielded regions likewise may all have the same longitudinal dimension, or they may differ from each other. The pattern of detection regions and shielded regions defined by the spatial filter may be periodic or non-periodic, as desired.

Figure 12:
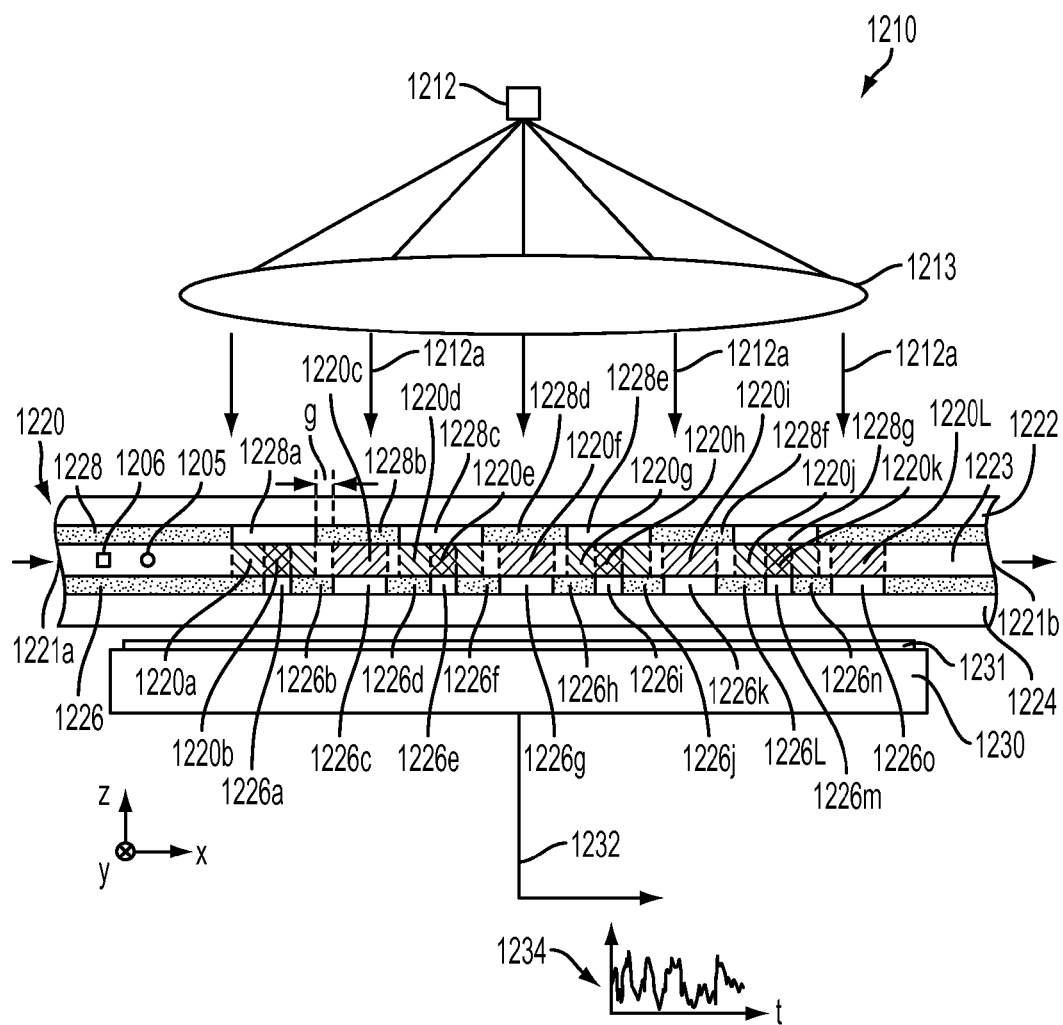
FIG. 12 is a schematic side or sectional view of another sample analyzer, illustrating repetitive, interspersed excitation and detection, and also illustrating second detection regions that overlap with excitation regions.

Turning now to FIG. 12, we see there a schematic view of another sample analyzer 1210. Like the analyzer 910 of FIG. 9, and unlike analyzers 110 of FIGS. 1 and 810 of FIG. 8, the analyzer 1210 utilizes repetitive, interspersed excitation and detection regions. However, unlike any of the analyzers 910, 810, or 110, the analyzer 1210 makes use of two different types of detection regions: first detection regions, which, like those of FIGS. 1, 8, and 9, do not overlap with any excitation region, and second detection regions which do overlap with one or more excitation region(s). The second detection regions may be provided to allow, in addition to detection of the first particles, detection of the second particles whose characteristic response time $\tau 2$ is less than that of the first particles.

The analyzer 1210 therefore incorporates a light source 1212, a fluid handling device 1220, a first spatial filter 1226, and a detector 1230. The analyzer 1210 also includes a second spatial filter 1228, which is used in combination with the light source 1212 to define a plurality of distinct excitation regions of the flow channel. The fluidic device 1220 is adapted to receive a sample of interest to be analyzed. The sample may enter the device 1220 at an inlet 1221a thereof and exit the device 1220 at an outlet 1221b thereof, flowing generally along the x-direction through a flow channel 1223 formed between confining members 1222, 1224. The members 1222, 1224 may be the same as or similar to other confining members discussed herein.

The light source 1212 may be the same as or similar to other excitation light sources discussed herein. The light source 1212 thus preferably emits excitation light in a light beam 1212a towards the fluidic device 1220. To facilitate this, an optical element 1213 such as one or more suitable lenses and/or mirrors may be used with or included in the light source. The excitation light 1212a may comprise light of a first wavelength $\lambda 1$, and in some cases, the excitation light may have a peak output at the wavelength $\lambda 1$. The spectral makeup or composition of the excitation light emitted by the source 1212 is preferably tailored to excite at least particles of a first type and particles of a second type that may be present in the sample.

The confining member 1222 transmits the light beam 1212a such that it illuminates the sample disposed within the flow channel 1223. The second spatial filter 1228 is interposed between the light source 1212 and the flow channel 1223, and its pattern of variable transmission operates to allow the light beam 1212a to illuminate only selected portions, referred to as excitation regions, of the flow channel 1223. The spatial filter 1228 is depicted as having transmitting portions 1228a, 1228c, 1228e, and 1228g arranged in alternating fashion with shielding portions 1228b, 1228d, 1228f. Other numbers of transmitting portions and shielding portions are of course also contemplated. The second spatial filter 1228 may be the same as or similar to other spatial filters discussed herein; thus, the second spatial filter may be monochromatic or polychromatic, it may be mounted in a remote or local configuration, its transmission function may be periodic or non-periodic, and it may have a desired minimum feature size MFS. In a simple case, the transmitting portions 1228a, 1228c, 1228e, and 1228g may all be completely clear, as in the case of apertures, and the shielding portions 1228b, 1228d, and 1228f may be completely opaque, as in the case of a layer of black ink or other absorptive, reflective, or scattering material. Light from the light beam 1212a passes through the transmitting portions of the second spatial filter to define distinct, spatially separated excitation regions 1220a, 1220c, 1220e, and 1220g of the flow channel 1223 as shown in the figure, with remaining regions of the flow channel preferably remaining substantially non-illuminated with the excitation light. As mentioned elsewhere herein, the second spatial filter may in some cases be omitted and replaced with one or more suitable optical elements that achieve the same result of spatially separated excitation regions.

The sample is depicted as containing two types of particles: first particles 1205, and second particles 1206. In the case of analyzer 1210, both the first particles 1205 and the second particles 1206 are assumed to be particles whose presence in the sample is sought to be detected and quantified by the analyzer. We assume that both the first particles 1205 and the second particles 1206 are excited by the excitation light 1212a, such that they emanate light, such emanating light typically propagating in all directions. In conventional analyzers, the light emitted by the second particles 1206 might ordinarily interfere with the detection of light emitted by the first particles 1205. The light emitted by the second particles might for example constitute relatively strong autofluorescence arising from particles or any other component of the sample, while the light emitted by the first particles might constitute a weaker fluorescent emission from particles such as cells that are tagged with a particular fluorescent dye. Consistent with our earlier discussion, we further assume that light emitted by the first particles has a characteristic first response time $\tau 1$, and that light emitted by the second particles has a characteristic second response time $\tau 2$, and that the first response time is greater than (i.e., longer than, or slower than) the second response time: $\tau 1 > \tau 2$. In some cases, the light emanating from the different particle types may differ from each other in other ways also, such as in their spectral characteristics.

Keeping in mind that the sample is pumped or otherwise drawn through the flow channel 1223 from the inlet 1221a to the outlet 1221b, particles in the sample will alternately pass through excitation regions and regions of the flow channel that are not illuminated with excitation light. As a given particle passes through a given excitation region, the particle becomes increasingly excited and gives off an increasing amount of emanating light. But when such particle exits the excitation region, the excitation decays, and the amount of emanating light also decays. This growth and decay in emanating light is made to repeat by providing the multiple transmitting portions in the spatial filter 1228, corresponding to the multiple excitation regions of the flow channel.

The analyzer also includes a detection channel comprising the combination of detector 1230 and first spatial filter 1226. An emission filter 1231 may also be provided as shown to block extraneous excitation light, and/or other undesired light, and transmit light emanating from particles of interest. The spatial filter 1226 comprises transmitting portions 1226a, 1226c, 1226e, 1226g, 1226i, 1226k, 1226m, and 1226o arranged in alternating fashion with shielding portions 1226b, 1226d, 1226f, 1226h, 1226j, 1226L, 1226n as shown in the figure. Other numbers of transmitting portions and shielding portions are of course also contemplated. The first spatial filter may be the same as or similar to other spatial filters discussed herein; thus, it may be monochromatic or polychromatic, it may be mounted in a remote or local configuration, its transmission function may be periodic or non-periodic, and it may have a desired minimum feature size MFS. In a simple case, the transmitting portions 1226a, 1226c, 1226e, 1226g, 1226i, 1226k, 1226m, and 1226o may all be completely clear, as in the case of apertures, and the shielding portions 1226b, 1226d, 1226f, 1226h, 1226j, 1226L, 1226n may be completely opaque, as in the case of a layer of black ink or other absorptive, reflective, or scattering material. The transmitting portions of the first spatial filter in combination with the placement of the detector 1230 define a plurality of distinct, spatially separated detection regions 1220b (which coincides or overlaps with a portion of excitation region 1220a), 1220c, 1220e (which coincides or overlaps with a portion of excitation region 1220d), 1220f, 1220h (which coincides or overlaps with a portion of excitation region 1220g), 1220i, 1220k (which coincides or overlaps with a portion of excitation region 1220j), and 1220L in the flow channel 1223: light emitted by an excited particle located in any of the detection regions passes through the corresponding transmitting portion of the first spatial filter and impinges on the active area of the photosensitive detector, producing an output signal on line 1232. On the other hand, light emitted by an excited particle located in any other portion of the flow channel 1223 may be substantially blocked from reaching the detector 1230 by the shielding portions of first spatial filter 1226. The detector 1230 may be the same as or similar to other photosensitive detectors discussed herein.

In the analyzer 1210, the first and second spatial filters are arranged and configured with respect to each other so that the excitation regions 1220a, 1220d, 1220g, 1220j are interspersed with the detection regions 1220b, 1220c, 1220e, 1220f, 1220h, 1220i, 1220k, and 1220L. Furthermore, the detection regions are made up of two different types of detection regions: first detection regions (1220c, 1220f, 1220i, and 1220L), which, like those of FIGS. 1, 8, and 9, do not overlap with any excitation region, and second detection regions (1220b, 1220e, 1220h, and 1220k) which do overlap with one or more excitation region(s). Furthermore, some portions of the excitation regions 1220a, 1220d, 1220g, 1220j are shielded from the detector 1230 by the first spatial filter 1226, while other portions of these excitation regions are not shielded from the detector. With this arrangement, the detector 1230 is responsive both to excited particles whose emanating light is decaying in strength due to the substantial absence of excitation light in the first detection regions, and to excited particles whose emanating light is growing in strength due to the presence of excitation light in the second detection regions.

Preferably, the first and second spatial filters are further arranged and configured with respect to each other to define a gap region at least between each excitation region and a neighboring downstream first detection region. Thus, with reference to FIG. 12, a gap region is preferably provided between excitation region 1220a and first detection region 1220c, and between excitation region 1220d and first detection region 1220f, and between excitation region 1220g and first detection region 1220i, and between excitation region 1220j and first detection region 1220L. Each gap region may be considered to extend from the downstream boundary of a given excitation region to an upstream boundary of the nearest downstream first detection region. These gap regions may be substantially identical in size and shape (and longitudinal length), or they may be somewhat different from each other. Preferably, each of these gap regions has a longitudinal dimension "g" (see FIG. 12) that is long enough so that light emanating from a given second particle has decreased to a negligible intensity or flux, even at the fastest operational flow speed (smax), at the moment such second particle enters a given first detection region. This condition may be expressed as g>τ2*smax. However, the dimension g of each of the gap regions is also preferably short enough so that light emanating from a given first particle has an intensity or flux that is relatively high, even at the slowest operational flow speed (smin), at the moment such first particle enters a given first detection region. This condition may be expressed as g<τ1*smin. Moreover, each first detection region preferably has a longitudinal dimension or length that is short enough so that light emanating from a given first particle is relatively high (e.g. is maintained above a minimum threshold level), even at the slowest operation flow speed (smin), throughout the time that such particle is present in such detection region. This latter condition may be expressed as Lmax<2*τ1*smin, where Lmax represents the maximum length of any of the individual first detection regions. (In cases where the first detection regions all have the same longitudinal length, then Lmax represents the length of each detection region.)

Similar to the analyzer design of FIG. 9, we see that by employing repetitive, interspersed excitation and detection regions (such as in the embodiment of FIG. 12), the analyzer of FIG. 12 can accommodate slower flow speeds, faster (shorter) characteristic response times τ1, and/or a longer overall detection zone (or longer overall spatial filter) than can be accommodated using a single unitary excitation region such as those of FIGS. 1 and 8. This is because in the design of FIG. 12, the emanating light from a given first particle only needs to remain at measurable levels (e.g. above a minimum threshold level) over the longitudinal span of one of the first detection regions, rather than over the longitudinal span of the detection zone which encompasses the entire set of detection regions. Thus, because of the interspersed excitation and detection, the relationship between L1 (the length along the flow channel of the collective set of all detection regions defined by the first spatial filter) and τ1 is no longer important. For example, L1 need not be less than 2*τ1*smin.

However, unlike the analyzers of FIGS. 1, 8, and 9, the analyzer 1210 produces a time-varying detector output resulting not only from excited particles of the first particle type, but also from excited particles of the second particle type. As an excited first particle 1205 passes through the flow channel 1223, it passes through multiple spatially separated detection regions, in which emanating light is transmitted through a given one of the transmitting portions of the first spatial filter 1226 to the detector 1230, and it passes through shielded regions, in which emanating light is at least partially blocked from the detector 1230 by a given one of the shielding portions of the first spatial filter 1226. The alternating transmitting and blocking of the emanating light produces a time variation in the detector output 1232. An excited second particle 1206 may also substantially contribute to the detector output 1232 and its time variation, due to the presence of the second detection regions (1220b, 1220e, 1220h, 1220k): in these second detection regions, emanating light from the excited second particle 1206 can pass through a given one of the transmitting portions of the first spatial filter 1226 to the detector 1230, even though emanating light from the second particle has decayed to negligible levels when the second particle 1206 is located in any of the first detection regions (1220c, 1220f, 1220i, 1220L) by virtue of the sufficient time delay produced by the gap between the given first detection region and the nearest upstream excitation region. An exemplary (idealized) time-varying output signal 1234 is shown in FIG. 12. A signal processing unit, as discussed elsewhere herein, can be used to evaluate the detector output signal, and provide a measure of at least the first particles in the sample based on the evaluation. In this embodiment, both fluorescence components are measured and included in the time-varying output signal. Therefore typically also both components are used to extract particle information. As mentioned above, both particle types (with their associated response times τ1 and τ2) can be associated with the same physical body, e.g., as a tagged fluorescence signal and a native fluorescence or scatter signal. In this case the fast decaying signal can be used to extract additional information, provide additional confirmation, and/or it can used as a trigger to start a refined data evaluation.

Figure 13:
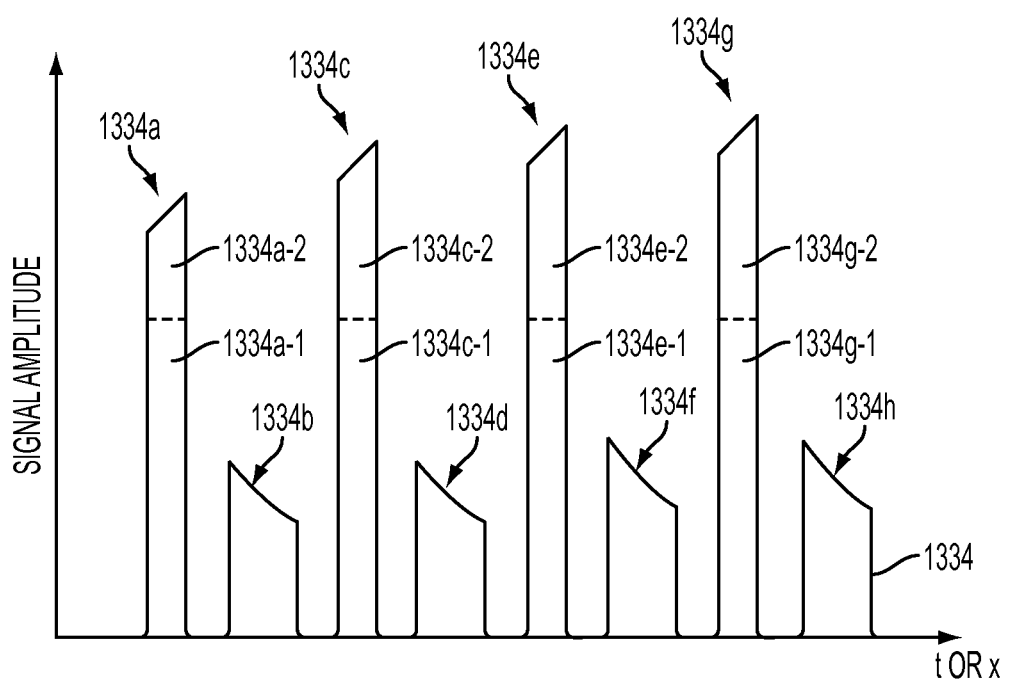
FIG. 13 is a graph of an idealized detector output associated with a detection event of a first particle and a second particle using an analyzer similar to that of FIG. 12.

Idealized depictions of intensity or flux as a function of time or position, and detector output as a function of time or position, for the analyzer 1210 of FIG. 12, can be seen in FIGS. 10 and 13, respectively.

FIG. 10 was described above as a graph of idealized functions of intensity or flux versus time or position for different particle types that may be present in the sample to be analyzed by the analyzer of FIG. 9. However, due to the similarity of the light source 912, the light beam 912a, the second spatial filter 928 with its constituent transmitting and shielding portions, and the flow channel 923 with its excitation regions 920a, 920c, 920e, and 920g and its gap regions, with corresponding elements of the analyzer 1210, the idealized curves 1007 and 1008 may be considered as also representing the relative intensity of light emanating from respective first and second particles 1205, 1206 of FIG. 12. Thus, as a first particle 1205 passes through the flow channel 1223, it may emanate light according to the idealized curve 1007, where the regions 1026a, 1026c, 1026e, and 1026g of the graph correspond to first detection regions 1220c, 1220f, 1220i, 1220L respectively. And as a second particle 1206 passes through the flow channel 1223, it may emanate light according to the idealized curve 1008, where the roughly rectangular-shaped features 1028a, 1020c, 1028e, 1028g correspond to the excitation regions 1220a, 1220d, 1220g, 1220j, respectively.

Only some of the emanating light represented in FIG. 10 is sensed by the detector 1230, due to the selective shielding effect of the first spatial filter 1226. In particular, only emanating light occurring in the first detection regions (1220c, 1220f, 1220i, 1220L) and in the second detection regions (1220b, 1220e, 1220h, 1220k) of the flow channel 1223, is sensed by the detector 1230. The result is an idealized detector output signal 1334 depicted schematically in FIG. 13.

The idealized signal 1334 is associated with a detection event of both a first particle 1205 and a second particle 1206 using an analyzer similar to that of FIG. 12, and the signal 1334 is sensitive to the presence both of these types of particles in the sample. The vertical axis of the graph of FIG. 13 represents the detector output in arbitrary units. The horizontal axis of the graph may be substantially the same as those of FIGS. 10 and 11. Inspection of the signal 1334 reveals that it is the same as or similar to the signal 1134 of FIG. 11, with signal portions 1334b, 1334d, 1334f, 1334h corresponding respectively to signal portions 1134a, 1134c, 1134e, 1134g (and also corresponding respectively to first detection regions 1220c, 1220f, 1220i, 1220L of flow channel 1223), except that the signal 1334 also includes additional signal portions 1334a, 1334c, 1334e, 1334g corresponding to the second detection regions (1220b, 1220e, 1220h, 1220k) of the flow channel 1223. The signal portions 1334b, 1334d, 1334f, 1334h preferably substantially track the intensity of flux of the first particle 1205 as it decays with time in the first detection regions, with substantially no contribution from the second particle 1206. In contrast, the signal portions 1334a, 1334*c*, 1334*e*, 1334*g* preferably substantially track the combined emission from the excited first particle 1205 (see signal portions 1334*a*-2, 1334*c*-2, 1334*e*-2, 1334*g*-2) and the excited second particle 1206 (see signal portions 1334*a*-1, 1334*c*-1, 1334*e*-1, 1334*g*-1). The signal 1334 is thus a composite of signal contributions from the first particle and signal contributions from the second particle. Due to the nature of the first and second detection regions, the signal contributions from the first particle occur at a greater frequency in the time-varying detector output signal than the signal contributions from the second particle. These differences in signal frequencies can be exploited by the signal processing unit to distinguish the detection event of a first particle from the detection event of a second particle.

Of course, the particular idealized signal 1334 shown in FIG. 13 is only exemplary and should not be construed to be limiting. The relative widths and spacings of the various labeled signal portions and of the various zero-level signal portions can be adjusted as desired by appropriate configuration of the first spatial filter 1226. The first spatial filter may be configured to define more or fewer than four distinct first detection regions, more or fewer than four distinct second detection regions, and more or fewer than seven shielded regions, in the flow channel. The first and second detection regions may all have the same longitudinal dimension, or they may differ from each other. The shielded regions likewise may all have the same longitudinal dimension, or they may differ from each other. The pattern of first detection regions, second detection regions, and shielded regions defined by the spatial filter may be periodic or non-periodic, as desired.

Figure 14:
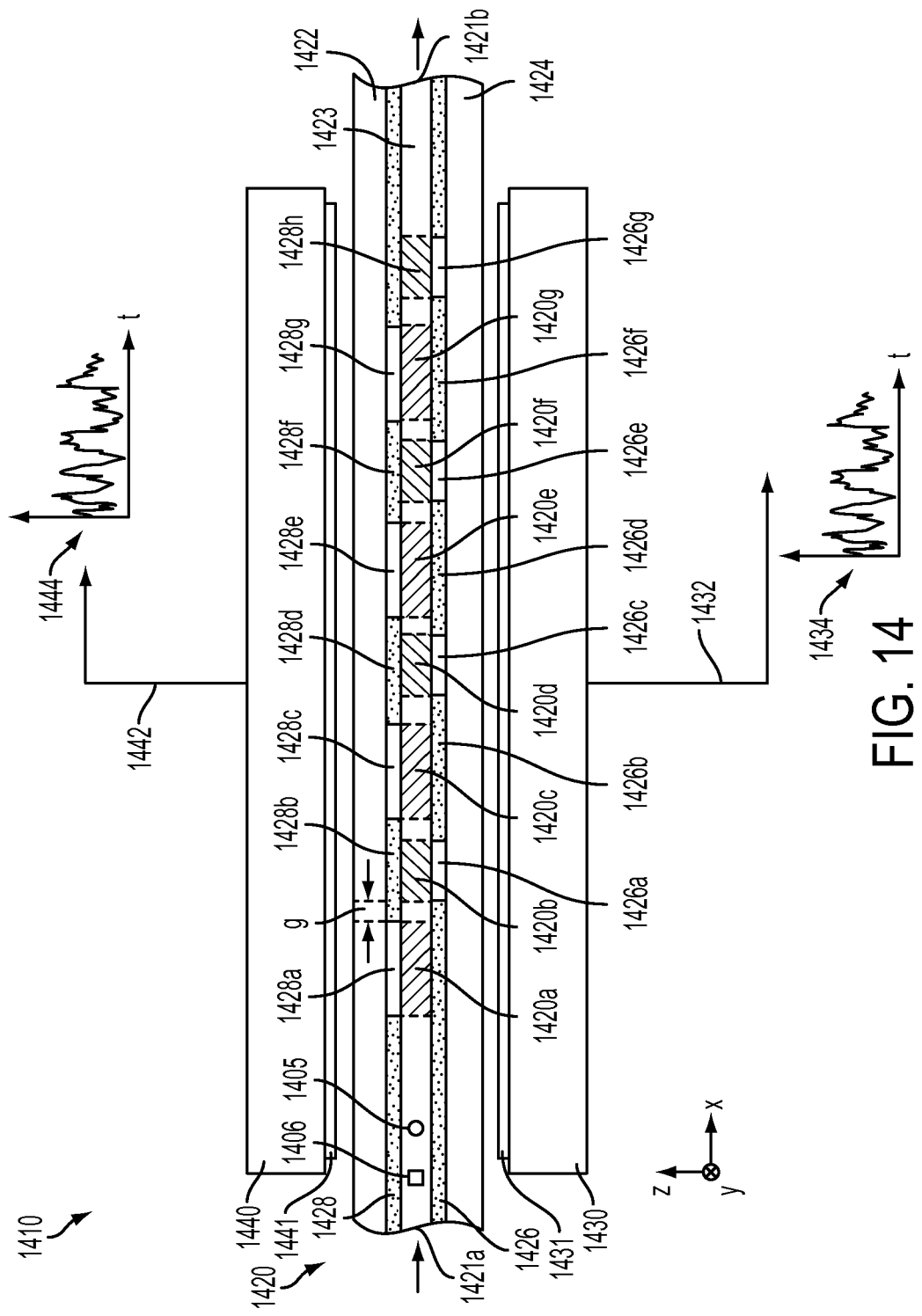
FIG. 14 is a schematic side or sectional view of another sample analyzer, illustrating repetitive, interspersed excitation and detection, and also illustrating two independent detector/spatial filter combinations, and also illustrating second detection regions that overlap with, and that may coincide with, excitation regions.

FIG. 14 is a schematic view of another sample analyzer 1410, illustrating repetitive, interspersed excitation and detection, and also illustrating two independent detector/spatial filter combinations, and also illustrating second detection regions that overlap with, and that may coincide with, excitation regions. In one embodiment, the analyzer 1410 may be substantially the same as analyzer 910 of FIG. 9, except that a second detector channel is added, the second detector channel being responsive only to excited particles that reside in the spatially separated excitation regions of the flow channel. The first detector channel of analyzer 1410, e.g., composed of first detector 1430 and first spatial filter 1426, may be the same as or similar to the detector channel depicted in FIG. 9, while the second detector channel of analyzer 1410, e.g., composed of second detector 1440 and second spatial filter 1428, may be configured to be responsive to excited first particles 1405 and excited second particles 1406 resident in the excitation regions of the flow channel 1423. Thus, similar to the analyzer 1210, the analyzer 1410 makes use of two different types of detection regions: first detection regions, which do not overlap with any excitation region, and second detection regions which do overlap with one or more excitation region(s). The second detection regions may be provided to allow, in addition to detection of the first particles, detection of the second particles whose characteristic response time $\tau 2$ is less than that of the first particles.

The analyzer 1410 therefore incorporates a light source (not shown) with an associated spatial filter (not shown), a fluid handling device 1420, a first spatial filter 1426, and a first detector 1430. The analyzer 1410 also includes a second spatial filter 1428, which is used in combination with a second detector 1440. The fluidic device 1420 is adapted to receive a sample of interest to be analyzed. The sample may enter the device 1420 at an inlet 1421*a* thereof and exit the device 1420 at an outlet 1421*b* thereof, flowing generally along the x-direction through a flow channel 1423 formed between confining members 1422, 1424. The members 1422, 1424 may be the same as or similar to other confining members discussed herein.

The light source in combination with its associated spatial filter (not shown), which may for example be disposed above or below the x-z plane of the figure, cooperate to define a plurality of distinct excitation regions 1420*a*, 1420*c*, 1420*e*, 1420*g* of the flow channel. The light source may be the same as or similar to other excitation light sources discussed herein. The light source thus preferably emits excitation light in a light beam towards the fluidic device 1420. To facilitate this, an optical element such as one or more suitable lenses and/or mirrors may be used with or included in the light source. The excitation light may comprise light of a first wavelength $\lambda 1$, and in some cases, the excitation light may have a peak output at the wavelength $\lambda 1$. The spectral makeup or composition of the excitation light emitted by the source is preferably tailored to excite at least particles of a first type and particles of a second type that may be present in the sample.

One or both confining members may transmit the light beam such that it illuminates the sample disposed within the flow channel 1423. The spatial filter (not shown) is interposed between the light source and the flow channel 1423, and its pattern of variable transmission operates to allow the light beam to illuminate only selected portions, referred to as excitation regions, of the flow channel 1423. The spatial filter (not shown) may have four transmitting portions arranged in alternating fashion with three shielding portions in a manner similar to or the same as second spatial filter 1428. Other numbers of transmitting portions and shielding portions are of course also contemplated. The spatial filter (not shown) may be the same as or similar to other spatial filters discussed herein; thus, it may be monochromatic or polychromatic, it may be mounted in a remote or local configuration, its transmission function may be periodic or non-periodic, and it may have a desired minimum feature size MFS. In a simple case, its transmitting portions may all be completely clear, as in the case of apertures, and its shielding portions may be completely opaque, as in the case of a layer of black ink or other absorptive, reflective, or scattering material. Light from the light beam passes through the transmitting portions of the second spatial filter to define distinct, spatially separated excitation regions 1420*a*, 1420*c*, 1420*e*, and 1420*g* of the flow channel 1423 as shown in the figure, with remaining regions of the flow channel preferably remaining substantially non-illuminated with the excitation light. As mentioned elsewhere herein, the spatial filter (not shown) may in some cases be omitted and replaced with one or more suitable optical elements that achieve the same result of spatially separated excitation regions.

The sample is depicted as containing two types of particles: first particles 1405, and second particles 1406. In the case of analyzer 1410, both the first particles 1405 and the second particles 1406 are assumed to be particles whose presence in the sample is sought to be detected and quantified by the analyzer. We assume that both the first particles 1405 and the second particles 1406 are excited by the excitation light, such that they emanate light, such emanating light typically propagating in all directions. In conventional analyzers, the light emitted by the second particles 1406 might ordinarily interfere with the detection of light emitted by the first particles 1405. The light emitted by the second particles might for example constitute relatively strong autofluorescence arising from particles or any other component of the sample, while the light emitted by the first particles might constitute a weaker fluorescent emission from particles such as cells that are tagged with a particular fluorescent dye. As discussed elsewhere herein, emission from the second particle may be or include: fluorescence from a second particle different from the first particle, the second particle tagged with a short lifetime fluorescent tag; native fluorescence, scatter, etc. from particles other than the first particle, or from one or more fluid components, or from the fluidic chip; and fluorescence from a second particle that is the same physical body as the first particle, such body being tagged with a first fluorescent tag of long lifetime τ1 and a second fluorescent tag of short lifetime τ2, or such body being tagged with the first fluorescent tag of long lifetime τ1 and having a native fluorescence of short lifetime τ2. Consistent with our earlier discussion, we further assume that light emitted by the first particles has a characteristic first response time τ1, and that light emitted by the second particles has a characteristic second response time τ2, and that the first response time is greater than (i.e., longer than, or slower than) the second response time: τ1>τ2. In some cases, the light emanating from the different particle types may differ from each other in other ways also, such as in their spectral characteristics.

Keeping in mind that the sample is pumped or otherwise drawn through the flow channel 1423 from the inlet 1421a to the outlet 1421b, particles in the sample will alternately pass through excitation regions and regions of the flow channel that are not illuminated with excitation light. As a given particle passes through a given excitation region, the particle becomes increasingly excited and gives off an increasing amount of emanating light. But when such particle exits the excitation region, the excitation decays, and the amount of emanating light also decays. This growth and decay in emanating light is made to repeat by providing the multiple transmitting portions in the spatial filter (not shown) associated with the light source, corresponding to the multiple excitation regions of the flow channel.

The analyzer also includes a first detection channel comprising the combination of detector 1430 and first spatial filter 1426. An emission filter 1431 may also be provided as shown to block extraneous excitation light, and/or other undesired light, and transmit light emanating from particles of interest. The spatial filter 1426 comprises transmitting portions 1426a, 1426c, 1426e, 1426g arranged in alternating fashion with shielding portions 1226b, 1226d, 1226f as shown in the figure. Other numbers of transmitting portions and shielding portions are of course also contemplated. The first spatial filter may be the same as or similar to other spatial filters discussed herein; thus, it may be monochromatic or polychromatic, it may be mounted in a remote or local configuration, its transmission function may be periodic or non-periodic, and it may have a desired minimum feature size MFS. In a simple case, the transmitting portions 1426a, 1426c, 1426e, 1426g may all be completely clear, as in the case of apertures, and the shielding portions 1426b, 1426d, 1426f may be completely opaque, as in the case of a layer of black ink or other absorptive, reflective, or scattering material. The transmitting portions of the first spatial filter 1426 in combination with the placement of the first detector 1430 define a plurality of distinct, spatially separated first detection regions 1420b, 1420d, 1420f, 1420h in the flow channel 1423: light emitted by an excited particle located in any of these first detection regions passes through the corresponding transmitting portion of the first spatial filter 1426 and impinges on the active area of the first photosensitive detector 1430, producing an output signal on line 1432. On the other hand, light emitted by an excited particle located in any other portion of the flow channel 1423 may be substantially blocked from reaching the first detector 1430 by the shielding portions of first spatial filter 1426. The detector 1430 may be the same as or similar to other photosensitive detectors discussed herein.

In the analyzer 1410, the first spatial filter is arranged and configured with respect to the light source and its associated spatial filter so that the excitation regions 1420a, 1420c, 1420e, 1420g are interspersed with the first detection regions 1420b, 1420d, 1420f, 1420h. Furthermore, the first detection regions preferably do not overlap with any excitation region, and the excitation regions are all substantially shielded from the first detector 1430 by the first spatial filter 1426. With this arrangement, the detector 1430 is responsive to excited first particles 1405 whose emanating light is decaying in strength due to the substantial absence of excitation light in the first detection regions. Preferably, the first spatial filter 1426 is further arranged and configured to define a gap region at least between each excitation region and a neighboring downstream first detection region. Thus, with reference to FIG. 14, a gap region is preferably provided between excitation region 1420a and first detection region 1420b, and between excitation region 1420c and first detection region 1420d, and between excitation region 1420e and first detection region 1420f, and between excitation region 1420g and first detection region 1420h. Each gap region may be considered to extend from the downstream boundary of a given excitation region to an upstream boundary of the nearest downstream first detection region. These gap regions may be substantially identical in size and shape (and longitudinal length), or they may be somewhat different from each other. Preferably, each of these gap regions has a longitudinal dimension "g" (see FIG. 14) that is long enough so that light emanating from a given second particle has decreased to a negligible intensity or flux, even at the fastest operational flow speed (smax), at the moment such second particle enters a given first detection region. This condition may be expressed as $g>\tau2*smax$. However, the dimension g of each of the gap regions is also preferably short enough so that light emanating from a given first particle has an intensity or flux that is relatively high, even at the slowest operational flow speed (smin), at the moment such first particle enters a given first detection region. This condition may be expressed as $g<\tau1*smin$. Moreover, each first detection region preferably has a longitudinal dimension or length that is short enough so that light emanating from a given first particle is relatively high (e.g. is maintained above a minimum threshold level), even at the slowest operation flow speed (smin), throughout the time that such particle is present in such detection region. This latter condition may be expressed as $Lmax<2*\tau1*smin$, where Lmax represents the maximum length of any of the individual first detection regions. (In cases where the first detection regions all have the same longitudinal length, then Lmax represents the length of each detection region.)

The analyzer 1410 thus produces a time-varying detector output 1432 for the first detector 1430 that results from excited particles of the first particle type, but not substantially from excited particles of the second particle type. An exemplary (idealized) time-varying output signal 1434 is shown in FIG. 14. A signal processing unit, as discussed elsewhere herein, can be used to evaluate the first detector output signal, and provide a measure of at least the first particles in the sample based on the evaluation.

In addition to the first detection channel, the analyzer also includes a second detection channel comprising the combination of detector 1440 and second spatial filter 1428. An emission filter 1441 may also be provided as shown to block extraneous excitation light, and/or other undesired light, and transmit light emanating from particles of interest. Here, the optical emission filter may be considered to be more important than in embodiments such as that of FIG. 1 or 9, since here excitation regions overlap with detection regions. However, if the emanating light from the second particles is scattered light, the filter 1441 may be omitted. The spatial filter 1428 comprises transmitting portions 1428*a*, 1428*c*, 1428*e*, 1428*g* arranged in alternating fashion with shielding portions 1428*b*, 1428*d*, 1428*f* as shown in the figure. Other numbers of transmitting portions and shielding portions are of course also contemplated. The second spatial filter may be the same as or similar to other spatial filters discussed herein; thus, it may be monochromatic or polychromatic, it may be mounted in a remote or local configuration, its transmission function may be periodic or non-periodic, and it may have a desired minimum feature size MFS. In a simple case, the transmitting portions 1428*a*, 1428*c*, 1428*e*, 1428*g* may all be completely clear, as in the case of apertures, and the shielding portions 1428*b*, 1428*d*, 1428*f* may be completely opaque, as in the case of a layer of black ink or other absorptive, reflective, or scattering material. The transmitting portions of the second spatial filter 1428 in combination with the placement of the second detector 1440 define a plurality of distinct, spatially separated second detection regions 1420*a*, 1420*c*, 1420*e*, 1420*g* in the flow channel 1423, which second detection regions may substantially coincide with the excitation regions, and are thus labeled identically. Light emitted by an excited particle located in any of the second detection regions passes through the corresponding transmitting portion of the second spatial filter 1428 and impinges on the active area of the second photosensitive detector 1440, producing an output signal on line 1442. On the other hand, light emitted by an excited particle located in any other portion of the flow channel 1423 may be substantially blocked from reaching the second detector 1440 by the shielding portions of second spatial filter 1428. The second detector 1440 may be the same as or similar to other photosensitive detectors discussed herein.

In the analyzer 1410, the second spatial filter 1428 is arranged and configured with respect to the light source and its associated spatial filter so that the excitation regions 1420*a*, 1420*c*, 1420*e*, 1420*g* overlap with and coincide with the second detection regions 1420*a*, 1420*c*, 1420*e*, 1420*g*. With this arrangement, the second detector 1440 is responsive to both excited first particles 1405 and to excited second particles 1406, each of which emanate light in the combined excitation/detection regions 1420*a*, 1420*c*, 1420*e*, 1420*g*. The analyzer 1410 thus produces a time-varying detector output 1442 for the second detector 1440 that results from excited particles of the first particle type and from excited particles of the second particle type. An exemplary (idealized) time-varying output signal 1444 is shown in FIG. 14. A signal processing unit, as discussed elsewhere herein, can be used to evaluate the second detector output signal, and provide a measure of at least the first particles and the second particles in the sample based on the evaluation. Combined data evaluation of signal 1444, which is responsive to both the first and second particles, and signal 1434, which is responsive chiefly or exclusively to the first particles, allows extraction of information of both the first particles and the second particles in the sample.

Similar to the analyzer designs of FIGS. 9 and 12, we see that by employing repetitive, interspersed excitation and detection regions (such as in the embodiment of FIG. 14), the analyzer of FIG. 14 can accommodate slower flow speeds, faster (shorter) characteristic response times τ1, and/or a longer overall detection zone (or longer overall spatial filter) than can be accommodated using a single unitary excitation region such as those of FIGS. 1 and 8. This is at least in part because, in the first detector channel of FIG. 14, the emanating light from a given first particle only needs to remain at measurable levels (e.g. above a minimum threshold level) over the longitudinal span of one of the first detection regions, rather than over the longitudinal span of the detection zone which encompasses the entire set of detection regions. Thus, because of the interspersed excitation and detection, the relationship between L1 (the length along the flow channel of the collective set of all detection regions defined by the first spatial filter) and τ1 is no longer important. For example, L1 need not be less than 2*τ1*smin.

The analyzer 1410 produces a time-varying second detector output 1442 resulting not only from excited particles of the first particle type, but also from excited particles of the second particle type. An exemplary (idealized) time-varying output signal 1444 is shown in FIG. 14. A signal processing unit, as discussed elsewhere herein, can be used to evaluate the second detector output signal, and provide a measure of at least the first and second particles in the sample based on the evaluation.

Figure 15:
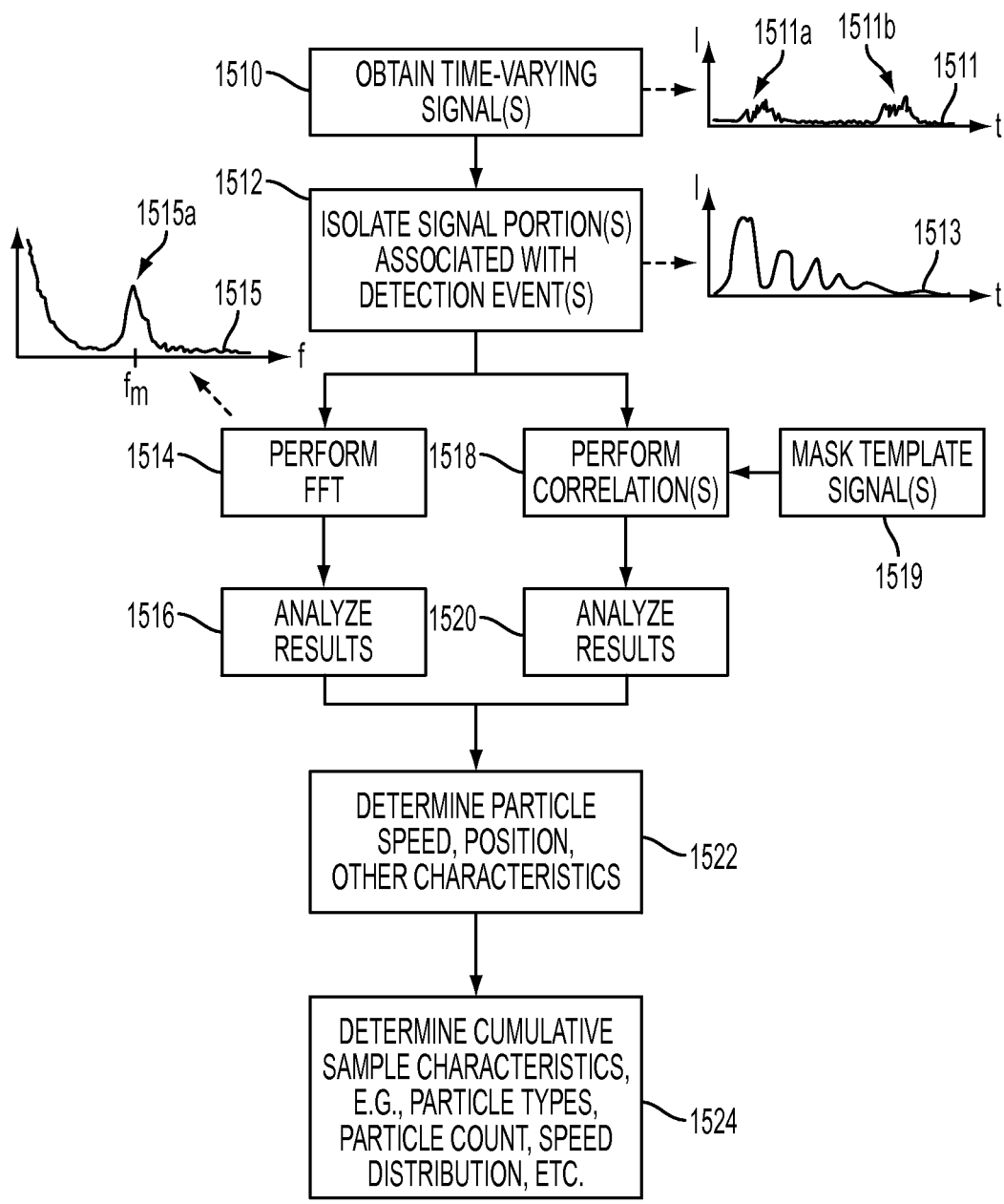
FIG. 15 is a flow diagram depicting a method that may be carried out with the disclosed analyzers.

In FIG. 15, we show a flow diagram of a method that may be used in at least some implementations of the disclosed sample analyzers. In box 1510, time-varying signal(s) are obtained from the photosensitive detector(s). (More than one detector may be used on a given analyzer, and each detector may have its own spatial filter, as discussed above.) A possible detector output signal 1511 is shown in a graph of intensity (I) versus time (t), the signal being representative of low particle concentrations (rare event detection) with sporadic signal bursts 1511*a*, 1511*b*. In box 1512, portions of each time-varying signal associated with detection events are isolated. This procedure may be important when dealing with rare event detection, since in those cases, the detector output may be substantially zero (e.g., at or near the noise floor) for significant periods of time, interrupted by sporadic signal bursts corresponding to a particle of interest passing through the detection portion of the flow channel, which we may refer to as a detection event for such particle. The portion of the time-varying signal corresponding to such a sporadic signal burst may be separated and isolated for individual evaluation and analysis. Such a signal portion 1513 is shown in a graph of intensity (I) versus time (t). Alternatively, even in cases involving high particle concentrations, where at least one particle is likely to be present in the detection portion of the flow channel at any given time, the continuous time-varying output signal of the detector may be subdivided into isolated signal portions of manageable size for signal processing purposes. The isolated signal portion may also represent a sliding time window of the continuous detector output, e.g., being constantly updated with the newest raw data points as the oldest raw data points are discarded.

After isolating the signal portion(s) in box 1512, different types of signal analysis can be performed on the signal portion. The different signal analysis types are shown as different branches of the flow diagram. Depending on the analyzer design and the particle(s) of interest, one may choose only one branch and one signal analysis type for a given signal portion, or one may choose multiple branches and multiple signal analysis types without limitation.

In box 1514, a frequency spectrum of each signal portion is calculated. The frequency spectrum may be calculated using a fast Fourier transform (FFT) technique, or by any other suitable technique. The hypothetical spectrum 1515 in the figure is representative of a signal portion containing information from a particle of interest, such as a particle of the first particle type, the spectrum 1515 containing a major frequency component 1515*a* at a mask frequency $f_m$. Assuming the spatial filter for the detector channel has a periodic (or quasi-periodic) transmission function, the mask frequency $f_m$ equals the speed of the particle (e.g. in units of meters/second) multiplied by the spatial frequency (e.g. in units of cycles/meter) of the spatial filter. Thus, if the spatial frequency of the spatial filter is known, the particle speed can be readily calculated based on the measured mask frequency $f_m$. In some cases, the calculated frequency spectrum 1515 may contain more than one local maximum or peak, e.g. where the spatial filter is or comprises a color mask and where different particles of interest such as a first particle and a third particle are present in the flow channel at the same time and emit light over different spectral ranges corresponding to different spatial frequencies of the color mask, or where a first particle of long response time $\tau 1$ and a second particle of short response time $\tau 2$ are detected together, as described in connection with FIGS. 12 and 13. In addition to calculation of the frequency spectrum, some analysis may be carried out in box 1516. Local maxima or peaks, and/or a dominant peak, in the frequency spectrum may be identified, and their coordinates in amplitude and frequency may be measured and stored. The amplitude of the frequency spectrum may also be measured at one or more predetermined frequencies. The measured amplitudes may be compared to each other and/or to one or more threshold values, e.g., so as to distinguish from the noise floor or to distinguish small signal levels from large signal levels. Ratios of the amplitudes may also be calculated.

In box 1518, correlations may be performed on the signal portion of the detector output. For example, the correlation between the signal portion and one or more template signals, shown schematically in box 1519, may be calculated. One template signal may, for example, be representative of the transmission function of a spatial filter. If the spatial transmission function (and hence also the template signal) of the spatial filter is non-periodic, this correlation of the signal portion with the template signal can be used to determine the longitudinal position of the particle in the flow channel. Further analysis of the correlation results may be carried out in box 1520.

After analyzing the frequency content of the signal portion and/or analyzing the correlation of the signal portion with known functions, the particle speed, position, and/or other characteristics can be calculated in box 1522. The absolute or relative amplitude of the signal associated with a given detected particle, e.g., the amplitude or magnitude of a frequency peak in the calculated frequency spectrum or the amplitude or magnitude of the correlation from the computed correlation, may be indicative of particle size or particle type or sub-type. For example, particles having the same characteristic response time $\tau 1$ may produce different signal amplitudes due to size differences or other differences.

In box 1524, cumulative sample information that has been extracted from numerous signal portions of the detector output may be tabulated and compiled. A count of particles may be maintained of the different particle types being identified, and results of particle speed, position, size, and other information may be compiled and analyzed.

Figure 16:
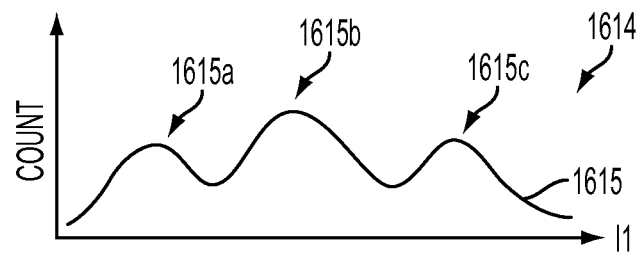
FIG. 16 is a graph containing hypothetical data that may be obtained using the disclosed analyzers and methods.

FIG. 16 is a graph 1614 that shows how data obtained using the disclosed analyzers and methods can be analyzed and evaluated. In the graph, hypothetical curve 1615 plots the number of occurrences (referred to as the "count") of amplitude or magnitude measurements I1 in a given detector channel, over a period of time that may encompass tens, hundreds, or thousands of individual detection events, e.g., all detection events associated with a given test sample. The I1 coordinate may be plotted on a linear scale or a logarithmic scale as desired. The coordinate I1 may be, for example, the magnitude of the frequency spectrum at the mask frequency $f_m$, or the correlation value of the relevant signal portion of the detector output with a mask template or other known signal. Inspection of the hypothetical curve 1615 shows that the (hypothetical) sample contains three distinct particle types, forming clusters or groups 1615a, 1615b, and 1615c. These groups are located along the I1 axis. We see in graph 1614 that distinctions between particle types or subtypes can be made based on the strength or magnitude of the response signal. Particles in the groups 1615a, 1615b, 1615c may, for example, all be detected by a given detector channel, but particles in the group 1615c provide a stronger signal, whether as a result of having a larger particle size or for other reasons, than particles in the group 1615b, and particles in the group 1615b provide a stronger signal than particles in the group 1615a. Stronger signals produce a greater magnitude in the I1 coordinate, hence, the group 1615c is shifted along the I1 axis relative to the group 1615b, and the group 1615b is shifted along the I1 axis relative to the group 1615a. Specific boundary conditions can be established to provide three clearly defined regions of the graph corresponding to the different groups, and the number of datapoints falling within the respective defined regions can provide a count of the three different particle types in the sample. In some cases, any single one of the groups 1615a, 1615b, 1615c may represent not just one particle type but multiple particle types, e.g., a population of small particles and a population of large particles, that yield similar I1 values. Additional mathematical analysis can in some cases be used to differentiate such similar particle types or populations also.

In some cases, e.g. where multiple detection channels are employed, two or more amplitude measurements may be obtained for each detected particle in the sample. For example, in the analyzer of FIG. 14, a given particle may produce one signal amplitude in the output of detector 1440, and a different signal amplitude in the output of detector 1430. In such cases, groups of datapoints may be defined in a 2-dimensional coordinate space (e.g. a first amplitude I1 and a second amplitude I2), or a 3-dimensional coordinate space, or more generally in an n-dimensional coordinate space, where n is the number of different amplitude measurements provided by the analyzer for each detected particle. Furthermore, analyzers such as those shown in FIGS. 1 and 8, if used in combination with a patterned color mask, can provide two or more signal amplitude measurements, allowing for 2, 3 or more dimensional coordinate space. In such cases, only one time-varying detector signal may be provided, but different correlations, anti-correlations, or other measurements can be performed on the signal to produce different signal amplitude measurements associated with different particle types. Reference in this regard is made to pending U.S. Publication No. 2011/0222062.

Figure 17:
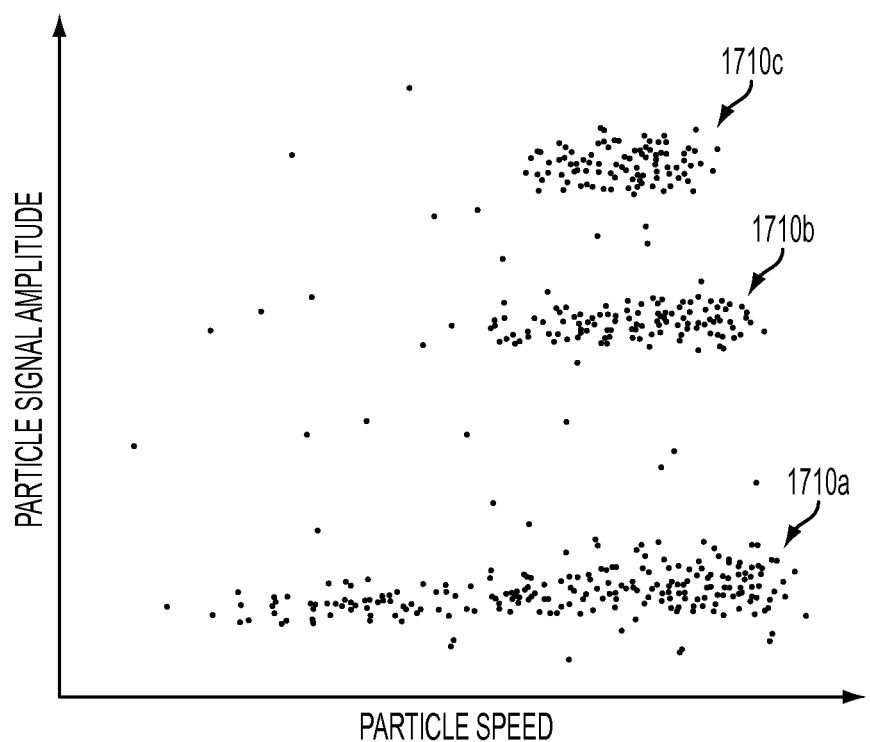
FIG. 17 is a velocity profile graph that plots particle signal amplitude versus particle speed, the graph containing hypothetical data.

Besides signal amplitude in the various channels, the speed of a given particle can also be computed based on a measurement of the mask frequency $f_m$ as discussed above. This information can be combined with signal amplitude characteristics to provide further insight regarding particle characteristics of the sample. FIG. 17 is a velocity profile graph that plots particle signal amplitude, such as the coordinate I1 in FIG. 16, versus particle speed. The graph again contains hypothetical datapoints representative of all, or at least some, of the particles detected in the sample under test. Inspection of the graph may reveal identifiable groups of particles, e.g. forming clusters or groups of datapoints 1710a, 1710b, and 1710c, which may correspond to the three groups 1615a, 1615b, 1615c in FIG. 16. Note that the speed information of each particle can also be used to modify the frequency spectrum (e.g. FFT) and/or correlation signals by making adjustments according to particle speed. Since slower particles reside in the detection area for longer times than faster particles, the slower particles tend to provide larger fluorescence signals and higher correlation values than faster particles. The signal processing unit of the measurement system may implement appropriate normalization or other adjustment of the frequency spectrum and/or correlation signals to correct for this effect.

Some of the above disclosure deals with the detection of a first particle type, having a relatively long response time $\tau 1$, and avoiding detection of a second particle type having a relatively short response time $\tau 2$, or, in some cases, detecting both the first and the second particle types. In some cases, particles of interest include a plurality of particle types at least two of which may have relatively long response times $\tau$, e.g., a third particle type of response time $\tau 3 > \tau 2$ and the first particle type with $\tau 1 > \tau 2$, with numerous possible permutations and relationships. Light emission from a particle type of interest may be based on tagging certain target particles with special bioprobes that exhibit a comparably long fluorescence life time. Such tagging techniques allow one to separate the particle signal of interest from scattered light and/or background fluorescent light having a much shorter fluorescent lifetime. As already described above, the tagged particles are excited and detected in spatially separated regions. When excited particles enter the detection region(s), scattered and/or auto fluorescence light has already disappeared or has been substantially reduced, which allows reliable detection of single dim particles of interest in even very large detection regions.

Examples of known bioprobes exhibiting relatively long fluorescence lifetimes include for instance Lanthanide fluorescent probes such as Europium, Terbium, and Samarium. Such fluorescent probes enable highly sensitive assays because their fluorescence lifetime ($\tau$ typically in a range from a few microseconds to milliseconds) is much longer than the lifetime of autofluorescence, which is typically in the few nanoseconds to a few tens of nanoseconds range. Table 1 lists some typical lifetimes and other features of exemplary long lifetime probes along with fluorescein isothiocyanate (FITC), which is a shorter lifetime fluorescence tag. The reader will understand that the invention is by no means limited to the listed probes, but can be used with any bioprobes or other substances or agents now known or later developed that satisfy the conditions set forth broadly in the foregoing description.

TABLE 1

|  | FITC | Lanthanide complex e.g., BHHCT-Eu | Polysterene Ln dots e.g., Fluoro-Max Europium | Silica Ln dots e.g., APS-BHHCT-Eu |
|---|---|---|---|---|
| Excitation (nm) | 450-530 | 310-370 | 310-370 | 310-370 |
| Lifetime (us) | 0.0045 | 380-640 | 720 | 370 |
| Size | ~400 Da | ~800 Da | ~100 nm | ~40 nm |

Target particles can be immuno-labeled with labels that have long lifetimes. Such a label could be made from lanthanide chelates that have lifetimes on the order of 500 microseconds to almost 1 ms, and can be excited with ~335 nm light. This lifetime is long compared to the autofluorescence, whose lifetime is typically much smaller than 100 ns. The labeled sample can be introduced into a micro-channel and caused to flow at an average speed of, for example, about 5 m/sec past an excitation source. Flow gradients in the microchannel may give rise to a range of operational flow speeds of particles through the flow channel. At a flow speed of 5 m/s, the autofluorescence is reduced to 36% of its initial value, i.e., reduced to 1/e, in about 0.5 micrometer of travel, while the labeled particles of interest may travel for, for example, 2.5 to 5 mm before their intensity is reduced to 1/e of their initial value.

Unless otherwise indicated, all numbers expressing feature sizes, amounts, physical properties, and so forth used in the specification and claims are to be understood as being modified by the term "about". Accordingly, unless indicated to the contrary, the numerical parameters set forth in the specification and claims are approximations that can vary depending on the desired properties sought to be obtained by those skilled in the art utilizing the teachings of the present application.

It will be appreciated that variants of the above-disclosed invention, and other features and functions, or alternatives thereof, may be combined into many other different systems or applications. Various presently unforeseen or unanticipated alternatives, modifications, variations, or improvements therein may be subsequently made by those skilled in the art, and are intended to be encompassed by the following claims. All U.S. patents, published and unpublished patent applications, and other patent and non-patent documents referred to herein are incorporated by reference, to the extent they do not directly contradict the foregoing disclosure.

The invention claimed is:

1. An apparatus for analyzing a sample, comprising:
a flow channel through which the sample can pass;
a first light source adapted to illuminate one or more first excitation region(s) of the flow channel with first excitation light, the first excitation light adapted to stimulate a first light emission from particles of a first particle type, the first light emission having a characteristic first response time $\tau 1$;
a detector disposed to receive light from a plurality of first detection regions of the flow channel, the detector adapted to provide a detector output based on the received light; and
a spatial filter disposed between the flow channel and the detector, the spatial filter having a pattern of variable transmission such that (a) the first light emission from a given first particle of the first particle type is transmitted to the detector when the given first particle is disposed in any of the first detection regions of the flow channel, and (b) the first light emission from the given first particle is at least partially blocked from reaching the detector when the given first particle is disposed in any of a plurality of first shielded regions of the flow channel, the first shielded regions being interspersed with the first detection regions;
wherein the first detection regions are spatially separated from the first excitation region(s) by a gap having a first gap dimension;
wherein the apparatus is configured to isolate the first light emission from a second light emission emitted by a component in the sample when exposed to the first excitation light, the second light emission characterized by a second response time $\tau 2$; and
wherein the gap dimension is a function of $\tau 1$ and $\tau 2$.

2. The apparatus of claim 1, wherein the one or more first excitation region(s) is a single unitary excitation region.

3. The apparatus of claim 2, wherein the single unitary excitation region is separated from a nearest one of the first detection regions by the first gap dimension, wherein the apparatus is configured to pass the sample through the flow channel at a minimum operating speed smin, and wherein the first gap dimension is less than $\tau 1*smin$.

4. The apparatus of claim 3, wherein the apparatus is configured to pass the sample through the flow channel at a maximum operating speed smax, and wherein the first gap dimension is greater than $\tau 2*smax$.

5. The apparatus of claim 2, wherein the apparatus is configured to pass the sample through the flow channel at a minimum operating speed smin, wherein the first detection regions collectively span a length L1 along the flow channel, and wherein L1 is less than $2*\tau 1*smin$.

6. An apparatus for analyzing a sample, comprising:
a flow channel through which the sample can pass;
a first light source adapted to illuminate one or more first excitation region(s) of the flow channel with first excitation light, the first excitation light adapted to stimulate a first light emission from particles of a first particle type, the first light emission having a characteristic first response time $\tau 1$;
a detector disposed to receive light from a plurality of first detection regions of the flow channel wherein the one or more first excitation region(s) is a plurality of first excitation regions interspersed with the first detection regions, the detector adapted to provide a detector output based on the received light; and
a spatial filter disposed between the flow channel and the detector, the spatial filter having a pattern of variable transmission such that (a) the first light emission from a given first particle of the first particle type is transmitted to the detector when the given first particle is disposed in any of the first detection regions of the flow channel, and (b) the first light emission from the given first particle is at least partially blocked from reaching the detector when the given first particle is disposed in any of a plurality of first shielded regions of the flow channel, the first shielded regions being interspersed with the first detection regions;
wherein the first detection regions are spatially separated from the first excitation region(s) by a gap having a first gap dimension;
wherein the apparatus is configured to isolate the first light emission from a second light emission emitted by a component in the sample when exposed to the first excitation light, the second light emission characterized by a second response time $\tau 2$; and
wherein the gap dimension is a function of $\tau 1$ and $\tau 2$.

7. The apparatus of claim 6, wherein at least one of the first excitation regions is separated from a nearest one of the first detection regions by the first gap dimension, wherein the apparatus is configured to pass the sample through the flow channel at a minimum operating speed smin, and wherein the first gap dimension is less than $\tau 1*smin$.

8. The apparatus of claim 7, wherein the apparatus is configured to pass the sample through the flow channel at a maximum operating speed smax, and wherein the first gap dimension is greater than $\tau 2*smax$.

9. The apparatus of claim 6, wherein the first detection regions have respective longitudinal dimensions along the flow channel, a maximum value of such respective longitudinal dimensions being Lmax, wherein the apparatus is configured to pass the sample through the flow channel at a minimum operating speed smin, and wherein Lmax is less than $2*\tau 1*smin$.

10. The apparatus of claim 6, wherein the detector is further disposed to receive light from one or more second detection regions of the flow channel, the second detection regions being interspersed with the first detection regions and the first shielded regions, and wherein the pattern of variable transmission of the spatial filter is further configured such that the first light emission from the given first particle is transmitted to the detector if the given first particle is disposed in any of the second detection regions of the flow channel, and wherein the one or more second detection regions overlap with the plurality of first excitation regions.

11. The apparatus of claim 6, wherein the spatial filter is configured such that the first excitation regions are substantially fully shielded from the detector by the spatial filter.

12. The apparatus of claim 1, wherein the detector is a first detector and the spatial filter is a first spatial filter, and wherein the apparatus further comprising:
a second detector disposed to receive light from a plurality of second detection regions of the flow channel, the second detector adapted to provide a second detector output based on the received light; and
a second spatial filter disposed between the flow channel and the second detector, the second spatial filter having a second pattern of variable transmission such that (a) the second light emission from a given second particle of the second particle type is transmitted to the second detector if the given second particle is disposed in any of the second detection regions of the flow channel, and (b) the second light emission from the given second particle is at least partially blocked from reaching the second detector if the given second particle is disposed in any of a plurality of second shielded regions of the flow channel, the second shielded regions being interspersed with the second detection regions.

13. The apparatus of claim 12, wherein the second detection regions are spatially separated from the first excitation region(s).

14. The apparatus of claim 12, wherein the second detection regions at least partially overlap with the first excitation region(s).

15. A method of analyzing a sample, comprising:
passing the sample through a flow channel;
exposing the sample to excitation light in one or more first excitation region(s) of the flow channel, the excitation light being effective to stimulate a first light emission from particles of a first particle type in the sample, the first light emission having a characteristic first response time $\tau 1$;
transmitting the first light emission from a given first particle of the first particle type to a detector when the given first particle is disposed in any of a plurality of first detection regions of the flow channel, the first detection regions being spatially separated from the first excitation region(s); and
at least partially blocking the first light emission from the given first particle from reaching the detector when the given first particle is disposed in any of a plurality of first shielded regions of the flow channel, the first shielded regions being interspersed with the first detection regions;
wherein for the given first particle, the transmitting is initiated a delay time after an end of the exposing; and
wherein the method is configured to isolate the first light emission from a second light emission emitted by a component in the sample when exposed to the first excitation light, the second light emission characterized by a second response time $\tau 2$ shorter than $\tau 1$, and wherein the delay time is a function of $\tau 1$ and $\tau 2$.

16. The method of claim 15, wherein for the given first particle, the exposing occurs before the transmitting and the at least partially blocking.

17. The method of claim 16, wherein the delay time is less than $\tau 1$.

18. The method of claim 17, wherein the delay time is greater than $\tau 2$.

19. The method of claim 16, wherein for the given first particle, the transmitting occurs over a time period that begins when the transmitting begins and ends when the transmitting ends, and the time period is less than $2*\tau 1$.

20. The method of claim 15, wherein the one or more first excitation regions comprises a plurality of first excitation regions, and wherein for the given first particle, the exposing is interspersed with the transmitting and the at least partially blocking.

21. The method of claim 20, wherein the transmitting further comprises transmitting the first light emission from the given first particle to the detector when the given first particle is disposed in any of one or more second detection regions of the flow channel, the second detection regions being interspersed with the first detection regions and the first shielded regions, and the one or more second detection regions overlapping with the plurality of first excitation regions.

22. The method of claim 15, further comprising:
transmitting the second light emission from a given second particle of the second particle type to a second detector when the given second particle is disposed in any of a plurality of second detection regions of the flow channel; and
at least partially blocking the second light emission from the given second particle from reaching the second detector when the given second particle is disposed in any of a plurality of second shielded regions of the flow channel, the second shielded regions being interspersed with the second detection regions.

* * * * *